US011180812B2

(12) United States Patent
Lyden et al.

(10) Patent No.: US 11,180,812 B2
(45) Date of Patent: Nov. 23, 2021

(54) USE OF DNA IN CIRCULATING EXOSOMES AS A DIAGNOSTIC MARKER FOR METASTATIC DISEASE

(71) Applicants: CORNELL UNIVERSITY, Ithaca, NY (US); SLOAN-KETTERING INSTITUTE FOR CANCER RESEARCH, New York, NY (US)

(72) Inventors: David C. Lyden, New York, NY (US); Hector Peinado Selgas, New York, NY (US); Haiying Zhang, New York, NY (US); Jacqueline Bromberg, New York, NY (US)

(73) Assignees: CORNELL UNIVERSITY, Ithaca, NY (US); SLOAN-KETTERING INSTITUTE FOR CANCER RESEARCH, New York, NY (US)

( * ) Notice: Subject to any disclaimer, the term of this patent is extended or adjusted under 35 U.S.C. 154(b) by 191 days.

(21) Appl. No.: 14/422,102

(22) PCT Filed: Aug. 16, 2013

(86) PCT No.: PCT/US2013/055395
§ 371 (c)(1),
(2) Date: Feb. 17, 2015

(87) PCT Pub. No.: WO2014/028862
PCT Pub. Date: Feb. 20, 2014

(65) Prior Publication Data
US 2015/0218651 A1 Aug. 6, 2015

Related U.S. Application Data

(60) Provisional application No. 61/794,384, filed on Mar. 15, 2013, provisional application No. 61/684,224, filed on Aug. 17, 2012.

(51) Int. Cl.
*C12Q 1/6886* (2018.01)
*G01N 33/574* (2006.01)

(52) U.S. Cl.
CPC ......... *C12Q 1/6886* (2013.01); *G01N 33/574* (2013.01); *C12Q 2600/106* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| 5,849,701 | A | 12/1998 | Roberts et al. |
| 7,147,852 | B2 | 12/2006 | Gilbertson |
| 7,511,056 | B2 | 3/2009 | Diefenbacher et al. |
| 8,158,589 | B2 | 4/2012 | Dotor Herrerias et al. |
| 8,569,462 | B2 | 10/2013 | Bedinger et al. |
| 8,691,944 | B2 | 4/2014 | Clark et al. |
| 9,816,998 | B2 | 11/2017 | Lyden et al. |
| 9,921,223 | B2 | 3/2018 | Kalluri et al. |
| 2003/0092019 | A1* | 5/2003 | Meyer .................... C07K 14/47 435/6.14 |
| 2010/0184046 | A1* | 7/2010 | Klass .................... C12Q 1/6886 435/7.1 |
| 2010/0196426 | A1* | 8/2010 | Skog .................... C12Q 1/6883 424/400 |
| 2011/0118298 | A1 | 5/2011 | Fritz et al. |
| 2011/0160210 | A1 | 6/2011 | Fleenor et al. |
| 2012/0208706 | A1 | 8/2012 | Downing et al. |
| 2013/0005599 | A1 | 1/2013 | Klass |
| 2013/0029339 | A1* | 1/2013 | Skog .................... C12Q 1/6858 435/6.12 |
| 2013/0177498 | A1 | 7/2013 | Goldenberg et al. |
| 2013/0287801 | A1 | 10/2013 | Castronovo et al. |
| 2014/0038901 | A1 | 2/2014 | Lyden et al. |
| 2014/0045915 | A1 | 2/2014 | Skog et al. |
| 2014/0162888 | A1 | 6/2014 | Kuslich et al. |
| 2014/0227179 | A1 | 8/2014 | Liu et al. |
| 2017/0175200 | A1 | 6/2017 | Lyden et al. |
| 2018/0045728 | A1 | 2/2018 | Kalluri et al. |
| 2018/0231558 | A1 | 8/2018 | Lyden et al. |
| 2019/0049435 | A1 | 2/2019 | Lyden et al. |

FOREIGN PATENT DOCUMENTS

| WO | 2005/091805 | 6/2005 |
| WO | 2009/100029 | 8/2009 |
| WO | 2010/056337 | 5/2010 |
| WO | 2010/141955 | 12/2010 |
| WO | 2010/141955 A2 | 12/2010 |
| WO | 2012/031008 A2 | 3/2012 |
| WO | 2012/135844 | 10/2012 |
| WO | 2013/028788 | 2/2013 |
| WO | 2013/134786 | 9/2013 |

(Continued)

OTHER PUBLICATIONS

Juppner (Bone 1995 vol. 17 No. 2 Supplement 39S-42S).*
Schmid et al. (Clin Cancer Research 2009 vol. 15 p. 4554).*
Adamczyk et al. (Life Sciences 2011 vol. 89 p. 304).*
Balaj et al. (Nature Communications 2010 vol. 2 p. 180) (Year: 2010).*

(Continued)

*Primary Examiner* — Katherine D Salmon
(74) *Attorney, Agent, or Firm* — Troutman Pepper Hamilton Sanders LLP (Rochester)

(57) ABSTRACT

The present invention is directed to methods of diagnosing, prognosing, and monitoring cancer in a subject. These methods involves selecting a subject having cancer, and obtaining, from the selected subject, a sample containing exosomal DNA. The presence or absence of one or more mutations in BRAF and/or EGFR is detected in the exosomal DNA sample from the subject, and a diagnosis and/or prognosis of the cancer is given based on the detection of the one or more mutations in BRAF and/or EGFR. The present invention further relates to methods of treating a subject having cancer and/or monitoring a subject response to therapy based on the detection of one or more mutations in BRAF and/or EGFR in the exosomal DNA sample.

6 Claims, 9 Drawing Sheets

Specification includes a Sequence Listing.

(56) References Cited

FOREIGN PATENT DOCUMENTS

| WO | 2014/028862 | 2/2014 |
|---|---|---|
| WO | 2014/037332 | 3/2014 |
| WO | 2014/055775 | 4/2014 |
| WO | 2014/062978 | 4/2014 |

OTHER PUBLICATIONS

PCT International Search Report and Written Opinion for corresponding International Application No. PCT/US2013/055395 (dated Dec. 16, 2013).
Guescini et al., "Astrocytes and Glioblastoma Cells Release Exosomes Carrying mtDNA," J Neural Transm 117(1):1-4 (2010).
Balaj et al., "Tumour Microvesicles Contain Retrotransposon Elements and Amplified Oncogene Sequences," Nat Commun 2:180 (2011).
Zhang et al., "Stimulated Human Mast Cells Secrete Mitochondrial Components That Have Autocrine and Paracrine Inflammatory Actions," PLOS ONE 7(12):1-9 (2012).
Kahlert et al., "Identification of Double-Stranded Genomic DNA Spanning Chromosomes with Mutated KRAS and p53 DNA in the Seram Exosomes of Patients with Pancreatic Cancer," J. Biol. Chem. 289(7):3869-3875 (2014).
Thakur et al., "Double-Stranded DNA in Exosomes: a Novel Biomarker in Cancer Detection," Cell Res. 24(6):766-769 (2014).
Batagov et al., "Exosomes Secreted by Human Cells Transport Largely mRNA Fragments that are Enriched in the 3'-Untranslated Regions," Biology Direct 8(12):1-8 (2013).
Fesler et al., "Circulating microRNA Testing for the Early Diagnosis and Follow-up of Colorectal Cancer Patients," Mol. Diagn. Ther. 18(3):303-308 (2014).
Mathivanan et al., "Exosomes: Extracellular Organelles Important in Intercellular Communication," J. Proteomics 73:1907-1920 (2010).
Zhang et al., "A Niche Role for Cancer Exosomes in Metastasis," Nat. Cell Biol. 17(6):709-711 (2015).
Seton-Rogers, "Metastasis: An Influential Delivery," Nat. Rev. Cancer 15(7):386 (2015).
Ferrarelli, "Exosomes Prep the Metastatic Site," Sci. Signal. 8(380):ec150 (2015).
Vignieri and Smith, "Cancer Biology: Tumor Cells Educate the Metastatic Niche," Science Magazine 348(6240):1220 (Jun. 12, 2015).
Ray, "Pancreatic Cancer Exosomes Prime the Liver for Metastasis," Nat. Rev. Gastroenterol. Hepatol. 12(7):371 (2015).
Costa-Silva et al., "Pancreatic Cancer Exosomes Initiate Pre-Metastatic Niche Formation in the Liver," Nat. Cell Biol. 17:816-826 (2015).
Hagemann et al., "Macrophages Induce Invasiveness of Epithelial Cancer Cells via NF-kappaB and JNK," J. Immunol. 175:1197-1205 (2005).
Desgrosellier et al., "Integrins in Cancer Biological Implications and Therapeutic Opportunities," Nat Rev Cancer 10(1):9-22 (2010).
Enns et al., "Alphavbeta5-integrins Mediate Early Steps of Metastasis Formation," Eur J Cancer 41(7):1065-1072 (2005).
Nair et al., "HYD1-induced Increase in Reactive Oxygen Species Leads to Autophagy and Necrotic Cell Death in Multiple Myeloma Cells," Mol Cancer Ther. 8(8):2441-2451 (2009).
Mullamitha et al., "Phase I Evaluation of a Fully Human Anti-Alphav Integrin Monoclonal Antibody (CNTO 95) in Patients With Advanced Solid Tumors," Clin. Cancer Res. 13(7):2128-2135 (2007).
Zimmer et al., "The S100 Protein Family: History, Function, and Expression," Brain Research Bulletin 37(4):417-429 (1995).

* cited by examiner

SEQUENCE LISTING

```
<160> NUMBER OF SEQ ID NOS: 17

<210> SEQ ID NO 1
<211> LENGTH: 766
<212> TYPE: PRT
<213> ORGANISM: Homo sapiens

<400> SEQUENCE: 1

Met Ala Ala Leu Ser Gly Gly Gly Gly Gly Ala Glu Pro Gly Gln
1               5                   10                  15

Ala Leu Phe Asn Gly Asp Met Glu Pro Glu Ala Gly Ala Gly Ala Gly
                20                  25                  30

Ala Ala Ala Ser Ser Ala Ala Asp Pro Ala Ile Pro Glu Glu Val Trp
            35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270
```

```
Ser Thr Glu Val Pro Leu Met Cys Val Asn Tyr Asp Gln Leu Asp Leu
            275                 280                 285

Leu Phe Val Ser Lys Phe Phe Glu His His Pro Ile Pro Gln Glu Glu
290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ala Pro Asn
            355                 360                 365

Val His Ile Asn Thr Ile Glu Pro Val Asn Ile Asp Asp Leu Ile Arg
370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser
            420                 425                 430

Glu Asp Arg Asn Arg Met Lys Thr Leu Gly Arg Arg Asp Ser Ser Asp
435                 440                 445

Asp Trp Glu Ile Pro Asp Gly Gln Ile Thr Val Gly Gln Arg Ile Gly
            450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
                500                 505                 510

Ile Leu Leu Phe Met Gly Tyr Ser Thr Lys Pro Gln Leu Ala Ile Val
            515                 520                 525

Thr Gln Trp Cys Glu Gly Ser Ser Leu Tyr His His Leu His Ile Ile
530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Asp Phe Gly Leu Ala Thr Val Lys Ser Arg Trp Ser Gly Ser His
            595                 600                 605

Gln Phe Glu Gln Leu Ser Gly Ser Ile Leu Trp Met Ala Pro Glu Val
610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
            660                 665                 670

Tyr Leu Ser Pro Asp Leu Ser Lys Val Arg Ser Asn Cys Pro Lys Ala
675                 680                 685
```

```
Met Lys Arg Leu Met Ala Glu Cys Leu Lys Lys Lys Arg Asp Glu Arg
        690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
                740                 745                 750

Thr Pro Ile Gln Ala Gly Gly Tyr Gly Ala Phe Pro Val His
            755                 760                 765

<210> SEQ ID NO 2
<211> LENGTH: 2949
<212> TYPE: DNA
<213> ORGANISM: Homo sapiens

<400> SEQUENCE: 2
```

| | | | | |
|---|---|---|---|---|
| cgcctccctt | cccctcccc | gcccgacagc | ggccgctcgg | gccccggctc tcggttataa | 60 |
| gatggcggcg | ctgagcggtg | gcggtggtgg | cggcgcggag | ccgggccagg ctctgttcaa | 120 |
| cggggacatg | gagcccgagg | ccggcgccgg | cgccggcgcc | gcggcctctt cggctgcgga | 180 |
| ccctgccatt | ccggaggagg | tgtggaatat | caaacaaatg | attaagttga cacaggaaca | 240 |
| tatagaggcc | ctattggaca | aatttggtgg | ggagcataat | ccaccatcaa tatatctgga | 300 |
| ggcctatgaa | gaatacacca | gcaagctaga | tgcactccaa | caaagagaac aacagttatt | 360 |
| ggaatctctg | gggaacggaa | ctgattttc | tgtttctagc | tctgcatcaa tggataccgt | 420 |
| tacatcttct | tcctcttcta | gcctttcagt | gctaccttca | tctctttcag ttttcaaaa | 480 |
| tcccacagat | gtggcacgga | gcaaccccaa | gtcaccacaa | aaacctatcg ttagagtctt | 540 |
| cctgcccaac | aaacagagga | cagtggtacc | tgcaaggtgt | ggagttacag tccgagacag | 600 |
| tctaaagaaa | gcactgatga | tgagaggtct | aatcccagag | tgctgtgctg tttacagaat | 660 |
| tcaggatgga | gagaagaaac | caattggttg | ggacactgat | atttcctggc ttactggaga | 720 |
| agaattgcat | gtggaagtgt | tggagaatgt | tccacttaca | acacacaact ttgtacgaaa | 780 |
| aacgttttc | accttagcat | tttgtgactt | ttgtcgaaag | ctgcttttcc agggtttccg | 840 |
| ctgtcaaaca | tgtggttata | aatttcacca | gcgttgtagt | acagaagttc cactgatgtg | 900 |
| tgttaattat | gaccaacttg | atttgctgtt | tgtctccaag | ttctttgaac caccccaat | 960 |
| accacaggaa | gaggcgtcct | tagcagagac | tgccctaaca | tctggatcat cccttccgc | 1020 |
| acccgcctcg | gactctattg | gcccccaaat | tctcaccagt | ccgtctcctt caaaatccat | 1080 |
| tccaattcca | cagcccttcc | gaccagcaga | tgaagatcat | cgaaatcaat ttgggcaacg | 1140 |
| agaccgatcc | tcatcagctc | ccaatgtgca | tataaacaca | atagaacctg tcaatattga | 1200 |
| tgacttgatt | agagaccaag | gatttcgtgg | tgatggagga | tcaaccacag gtttgtctgc | 1260 |
| taccccccct | gcctcattac | ctggctcact | aactaacgtg | aaagccttac agaaatctcc | 1320 |
| aggacctcag | cgagaaagga | agtcatcttc | atcctcagaa | gacaggaatc gaatgaaaac | 1380 |
| acttggtaga | cgggactcga | gtgatgattg | ggagattcct | gatgggcaga ttacagtggg | 1440 |
| acaaagaatt | ggatctggat | catttggaac | agtctacaag | ggaaagtggc atggtgatgt | 1500 |
| ggcagtgaaa | atgttgaatg | tgacagcacc | tacctcag | cagttacaag ccttcaaaa | 1560 |
| tgaagtagga | gtactcagga | aaacacgaca | tgtgaatatc | ctactcttca tgggctatt | 1620 |
| cacaaagcca | caactggcta | ttgttaccca | gtggtgtgag | ggctccagct tgtatcacca | 1680 |

-continued

```
tctccatatc attgagacca aatttgagat gatcaaactt atagatattg cacgacagac    1740
tgcacagggc atggattact tacacgccaa gtcaatcatc cacagagacc tcaagagtaa    1800
taatatattt cttcatgaag acctcacagt aaaaataggt gattttggtc tagctacagt    1860
gaaatctcga tggagtgggt cccatcagtt tgaacagttg tctggatcca ttttgtggat    1920
ggcaccagaa gtcatcagaa tgcaagataa aaatccatac agctttcagt cagatgtata    1980
tgcatttgga attgttctgt atgaattgat gactggacag ttaccttatt caaacatcaa    2040
caacagggac cagataattt ttatggtggg acgaggatac ctgtctccag atctcagtaa    2100
ggtacggagt aactgtccaa aagccatgaa gagattaatg gcagagtgcc tcaaaaagaa    2160
aagagatgag agaccactct tcccccaaat tctcgcctct attgagctgc tggcccgctc    2220
attgccaaaa attcaccgca gtgcatcaga accctccttg aatcgggctg gtttccaaac    2280
agaggatttt agtctatatg cttgtgcttc tccaaaaaca cccatccagg caggggata    2340 tggtgcgttt cctgtccact gaaacaaatg agtgagagag ttcaggagag tagcaacaaa    2400
aggaaaataa atgaacatat gtttgcttat atgttaaatt gaataaaata ctctcttttt    2460
ttttaaggtg aaccaaagaa cacttgtgtg gttaaagact agatataatt tttccccaaa    2520
ctaaaattta tacttaacat tggattttta acatccaagg gttaaaatac atagacattg    2580
ctaaaaattg gcagagcctc ttctagaggc tttactttct gttccgggtt tgtatcattc    2640
acttggttat tttaagtagt aaacttcagt ttctcatgca acttttgttg ccagctatca    2700
catgtccact agggactcca gaagaagacc ctacctatgc ctgtgtttgc aggtgagaag    2760
ttggcagtcg gttagcctgg gttagataag gcaaactgaa cagatctaat ttaggaagtc    2820
agtagaattt aataattcta ttattattct taataatttt tctataacta tttcttttta    2880
taacaatttg gaaaatgtgg atgtctttta tttccttgaa gcaataaact aagtttcttt    2940
ttataaaaa                                                            2949
```

<210> SEQ ID NO 3
<211> LENGTH: 1209
<212> TYPE: PRT
<213> ORGANISM: Homo sapiens

<400> SEQUENCE: 3

```
Arg Pro Ser Gly Thr Ala Gly Ala Ala Leu Leu Ala Leu Leu Ala Ala
1               5                   10                  15

Leu Cys Pro Ala Ser Arg Ala Leu Glu Glu Lys Lys Val Cys Gln Gly
                20                  25                  30

Thr Ser Asn Lys Leu Thr Gln Leu Gly Thr Phe Glu Asp His Phe Leu
            35                  40                  45

Ser Leu Gln Arg Met Phe Asn Asn Cys Glu Val Val Leu Gly Asn Leu
        50                  55                  60

Glu Ile Thr Tyr Val Gln Arg Asn Tyr Asp Leu Ser Phe Leu Lys Thr
65                  70                  75                  80

Ile Gln Glu Val Ala Gly Tyr Val Leu Ile Ala Leu Asn Thr Val Glu
                85                  90                  95

Arg Ile Pro Leu Glu Asn Leu Gln Ile Ile Arg Gly Asn Met Tyr Tyr
            100                 105                 110

Glu Asn Ser Tyr Ala Leu Ala Val Leu Ser Asn Tyr Asp Ala Asn Lys
        115                 120                 125

Thr Gly Leu Lys Glu Leu Pro Met Arg Asn Leu Gln Glu Ile Leu His
    130                 135                 140
```

-continued

```
Gly Ala Val Arg Phe Ser Asn Asn Pro Ala Leu Cys Asn Val Glu Ser
145                 150                 155                 160

Ile Gln Trp Arg Asp Ile Val Ser Ser Asp Phe Leu Ser Asn Met Ser
            165                 170                 175

Met Asp Phe Gln Asn His Leu Gly Ser Cys Gln Lys Cys Asp Pro Ser
                180                 185                 190

Cys Pro Asn Gly Ser Cys Trp Gly Ala Gly Glu Glu Asn Cys Gln Lys
            195                 200                 205

Leu Thr Lys Ile Ile Cys Ala Gln Gln Cys Ser Gly Arg Cys Arg Gly
        210                 215                 220

Lys Ser Pro Ser Asp Cys Cys His Asn Gln Cys Ala Ala Gly Cys Thr
225                 230                 235                 240

Gly Pro Arg Glu Ser Asp Cys Leu Val Cys Arg Lys Phe Arg Asp Glu
                245                 250                 255

Ala Thr Cys Lys Asp Thr Cys Pro Pro Leu Met Leu Tyr Asn Pro Thr
            260                 265                 270

Thr Tyr Gln Met Asp Val Asn Pro Glu Gly Lys Tyr Ser Phe Gly Ala
        275                 280                 285

Thr Cys Val Lys Lys Cys Pro Arg Asn Tyr Val Val Thr Asp His Gly
    290                 295                 300

Ser Cys Val Arg Ala Cys Gly Ala Asp Ser Tyr Glu Met Glu Glu Asp
305                 310                 315                 320

Gly Val Arg Lys Cys Lys Lys Cys Glu Gly Pro Cys Arg Lys Val Cys
                325                 330                 335

Asn Gly Ile Gly Ile Gly Glu Phe Lys Asp Ser Leu Ser Ile Asn Ala
            340                 345                 350

Thr Asn Ile Lys His Phe Lys Asn Cys Thr Ser Ile Ser Gly Asp Leu
        355                 360                 365

His Ile Leu Pro Val Ala Phe Arg Gly Asp Ser Phe Thr His Thr Pro
    370                 375                 380

Pro Leu Asp Pro Gln Glu Leu Asp Ile Leu Lys Thr Val Lys Glu Ile
385                 390                 395                 400

Thr Gly Phe Leu Leu Ile Gln Ala Trp Pro Glu Asn Arg Thr Asp Leu
                405                 410                 415

His Ala Phe Glu Asn Leu Glu Ile Ile Arg Gly Arg Thr Lys Gln His
            420                 425                 430

Gly Gln Phe Ser Leu Ala Val Val Ser Leu Asn Ile Thr Ser Leu Gly
        435                 440                 445

Leu Arg Ser Leu Lys Glu Ile Ser Asp Gly Asp Val Ile Ile Ser Gly
    450                 455                 460

Asn Lys Asn Leu Cys Tyr Ala Asn Thr Ile Asn Trp Lys Lys Leu Phe
465                 470                 475                 480

Gly Thr Ser Gly Gln Lys Thr Lys Ile Ile Ser Asn Arg Gly Glu Asn
                485                 490                 495

Ser Cys Lys Ala Thr Gly Gln Val Cys His Ala Leu Cys Ser Pro Glu
            500                 505                 510

Gly Cys Trp Gly Pro Glu Pro Arg Asp Cys Val Ser Cys Arg Asn Val
        515                 520                 525

Ser Arg Gly Arg Glu Cys Val Asp Lys Cys Asn Leu Leu Glu Gly Glu
    530                 535                 540

Pro Arg Glu Phe Val Glu Asn Ser Glu Cys Ile Gln Cys His Pro Glu
545                 550                 555                 560
```

```
Cys Leu Pro Gln Ala Met Asn Ile Thr Cys Thr Gly Arg Gly Pro Asp
                565                 570                 575

Asn Cys Ile Gln Cys Ala His Tyr Ile Asp Gly Pro His Cys Val Lys
            580                 585                 590

Thr Cys Pro Ala Gly Val Met Gly Glu Asn Asn Thr Leu Val Trp Lys
        595                 600                 605

Tyr Ala Asp Ala Gly His Val Cys His Leu Cys His Pro Asn Cys Thr
    610                 615                 620

Tyr Gly Cys Thr Gly Pro Gly Leu Glu Gly Cys Pro Thr Asn Gly Pro
625                 630                 635                 640

Lys Ile Pro Ser Ile Ala Thr Gly Met Val Gly Ala Leu Leu Leu Leu
            645                 650                 655

Leu Val Val Ala Leu Gly Ile Gly Leu Phe Met Arg Arg Arg His Ile
        660                 665                 670

Val Arg Lys Arg Thr Leu Arg Arg Leu Leu Gln Glu Arg Glu Leu Val
    675                 680                 685

Glu Pro Leu Thr Pro Ser Gly Glu Ala Pro Asn Gln Ala Leu Leu Arg
    690                 695                 700

Ile Leu Lys Glu Thr Glu Phe Lys Lys Ile Lys Val Leu Gly Ser Gly
705                 710                 715                 720

Ala Phe Gly Thr Val Tyr Lys Gly Leu Trp Ile Pro Glu Gly Glu Lys
                725                 730                 735

Val Lys Ile Pro Val Ala Ile Lys Glu Leu Arg Glu Ala Thr Ser Pro
            740                 745                 750

Lys Ala Asn Lys Glu Ile Leu Asp Glu Ala Tyr Val Met Ala Ser Val
        755                 760                 765

Asp Asn Pro His Val Cys Arg Leu Leu Gly Ile Cys Leu Thr Ser Thr
    770                 775                 780

Val Gln Leu Ile Thr Gln Leu Met Pro Phe Gly Cys Leu Leu Asp Tyr
785                 790                 795                 800

Val Arg Glu His Lys Asp Asn Ile Gly Ser Gln Tyr Leu Leu Asn Trp
                805                 810                 815

Cys Val Gln Ile Ala Lys Gly Met Asn Tyr Leu Glu Asp Arg Arg Leu
            820                 825                 830

Val His Arg Asp Leu Ala Ala Arg Asn Val Leu Val Lys Thr Pro Gln
        835                 840                 845

His Val Lys Ile Thr Asp Phe Gly Leu Ala Lys Leu Leu Gly Ala Glu
    850                 855                 860

Glu Lys Glu Tyr His Ala Glu Gly Gly Lys Val Pro Ile Lys Trp Met
865                 870                 875                 880

Ala Leu Glu Ser Ile Leu His Arg Ile Tyr Thr His Gln Ser Asp Val
                885                 890                 895

Trp Ser Tyr Gly Val Thr Val Trp Glu Leu Met Thr Phe Gly Ser Lys
            900                 905                 910

Pro Tyr Asp Gly Ile Pro Ala Ser Glu Ile Ser Ser Ile Leu Glu Lys
        915                 920                 925

Gly Glu Arg Leu Pro Gln Pro Pro Ile Cys Thr Ile Asp Val Tyr Met
    930                 935                 940

Ile Met Val Lys Cys Trp Met Ile Asp Ala Asp Ser Arg Pro Lys Phe
945                 950                 955                 960

Arg Glu Leu Ile Ile Glu Phe Ser Lys Met Ala Arg Asp Pro Gln Arg
                965                 970                 975
```

-continued

```
Tyr Leu Val Ile Gln Gly Asp Glu Arg Met His Leu Pro Ser Pro Thr
            980                 985                 990

Asp Ser Asn Phe Tyr Arg Ala Leu Met Asp Glu Glu Asp Met Asp Asp
        995                 1000                1005

Val Val Asp Ala Asp Glu Tyr Leu Ile Pro Gln Gln Gly Phe Phe
    1010                1015                1020

Ser Ser Pro Ser Thr Ser Arg Thr Pro Leu Leu Ser Ser Leu Ser
    1025                1030                1035

Ala Thr Ser Asn Asn Ser Thr Val Ala Cys Ile Asp Arg Asn Gly
    1040                1045                1050

Leu Gln Ser Cys Pro Ile Lys Glu Asp Ser Phe Leu Gln Arg Tyr
    1055                1060                1065

Ser Ser Asp Pro Thr Gly Ala Leu Thr Glu Asp Ser Ile Asp Asp
    1070                1075                1080

Thr Phe Leu Pro Val Pro Glu Tyr Ile Asn Gln Ser Val Pro Lys
    1085                1090                1095

Arg Pro Ala Gly Ser Val Gln Asn Pro Val Tyr His Asn Gln Pro
    1100                1105                1110

Leu Asn Pro Ala Pro Ser Arg Asp Pro His Tyr Gln Asp Pro His
    1115                1120                1125

Ser Thr Ala Val Gly Asn Pro Glu Tyr Leu Asn Thr Val Gln Pro
    1130                1135                1140

Thr Cys Val Asn Ser Thr Phe Asp Ser Pro Ala His Trp Ala Gln
    1145                1150                1155

Lys Gly Ser His Gln Ile Ser Leu Asp Asn Pro Asp Tyr Gln Gln
    1160                1165                1170

Asp Phe Phe Pro Lys Glu Ala Lys Pro Asn Gly Ile Phe Lys Gly
    1175                1180                1185

Ser Thr Ala Glu Asn Ala Glu Tyr Leu Arg Val Ala Pro Gln Ser
    1190                1195                1200

Ser Glu Phe Ile Gly Ala
    1205

<210> SEQ ID NO 4
<211> LENGTH: 5616
<212> TYPE: DNA
<213> ORGANISM: Homo sapiens

<400> SEQUENCE: 4
ccccggcgca gcgcggccgc agcagcctcc gcccccgca cggtgtgagc gcccgacgcg      60
gccgaggcgg ccggagtccc gagctagccc cggcggccgc cgccgcccag accggacgac     120
aggccacctc gtcggcgtcc gcccgagtcc ccgcctcgcc gccaacgcca caaccaccgc     180
gcacggcccc ctgactccgt ccagtattga tcgggagagc cggagcgagc tcttcgggga     240
gcagcgatgc gaccctccgg gacggccggg gcagcgctcc tggcgctgct ggctgcgctc     300
tgcccggcga gtcgggctct ggaggaaaag aaagtttgcc aaggcacgag taacaagctc     360
acgcagttgg cacttttga agatcatttt ctcagcctcc agaggatgtt caataactgt     420
gaggtggtcc ttgggaattt ggaaattacc tatgtgcaga ggaattatga tctttccttc     480
ttaaagacca tccaggaggt ggctggttat gtcctcattg ccctcaacac agtggagcga     540
attcctttgg aaaacctgca gatcatcaga ggaaatatgt actacgaaaa ttcctatgcc     600
ttagcagtct tatctaacta tgatgcaaat aaaaccggac tgaaggagct gcccatgaga     660
aatttacagg aaatcctgca tggcgccgtg cggttcagca acaaccctgc cctgtgcaac     720
```

```
gtggagagca tccagtggcg ggacatagtc agcagtgact ttctcagcaa catgtcgatg     780
gacttccaga accacctggg cagctgccaa aagtgtgatc caagctgtcc caatgggagc     840
tgctggggtg caggagagga gaactgccag aaactgacca aaatcatctg tgcccagcag     900
tgctccgggc gctgccgtgg caagtccccc agtgactgct gccacaacca gtgtgctgca     960
ggctgcacag gcccccggga gagcgactgc ctggtctgcc gcaaattccg agacgaagcc    1020
acgtgcaagg acacctgccc cccactcatg ctctacaacc ccaccacgta ccagatggat    1080
gtgaaccccg agggcaaata cagctttggt gccacctgcg tgaagaagtg tccccgtaat    1140
tatgtggtga cagatcacgg ctcgtgcgtc cgagcctgtg gggccgacag ctatgagatg    1200
gaggaagacg gcgtccgcaa gtgtaagaag tgcgaagggc cttgccgcaa agtgtgtaac    1260
ggaataggta ttggtgaatt taaagactca ctctccataa atgctacgaa tattaaacac    1320
ttcaaaaact gcacctccat cagtggcgat ctccacatcc tgccggtggc atttagggt     1380 gactccttca cacatactcc tcctctggat ccacaggaac tggatattct gaaaaccgta    1440
aaggaaatca cagggttttt gctgattcag cttggcctg aaaacaggac ggacctccat     1500
gcctttgaga acctagaaat catacgcggc aggaccaagc aacatggtca gttttctctt    1560
gcagtcgtca gcctgaacat aacatccttg ggattacgct ccctcaagga gataagtgat    1620
ggagatgtga taatttcagg aaacaaaaat ttgtgctatg caaatacaat aaactggaaa    1680
aaactgtttg gaacctccgg tcagaaaacc aaaattataa gcaacagagg tgaaaacagc    1740
tgcaaggcca caggccaggt ctgccatgcc ttgtgctccc ccgagggctg ctggggcccg    1800
gagcccaggg actgcgtctc ttgccggaat gtcagccgag gcagggaatg cgtggacaag    1860
tgcaaccttc tggagggtga gccaagggag tttgtggaga ctctgagtg catacagtgc    1920 cacccagagt gcctgcctca ggccatgaac atcacctgca caggacgggg accagacaac    1980
tgtatccagt gtgcccacta cattgacggc ccccactgcg tcaagacctg cccggcagga    2040
gtcatgggag aaaacaacac cctggtctgg aagtacgcag acgccggcca tgtgtgccac    2100
ctgtgccatc caaactgcac ctacggatgc actgggccag tcttgaagg ctgtccaacg     2160 aatgggccta agatcccgtc catcgccact gggatggtgg gggcctcct cttgctgctg     2220 gtggtggccc tggggatcgg cctcttcatg cgaaggcgcc acatcgttcg gaagcgcacg    2280
ctgcggagcc tgctgcagga gagggagctt gtggagcctc ttacacccag tggagaagct    2340
cccaaccaag ctctcttgag gatcttgaag gaaactgaat tcaaaaagat caaagtgctg    2400
ggctccggtg cgttcggcac ggtgtataag ggactctgga tcccagaagg tgagaaagtt    2460
aaaattcccg tcgctatcaa ggaattaaga gaagcaacat ctccgaaagc caacaaggaa    2520
atcctcgatg aagcctacgt gatggccagc gtggacaacc cccacgtgtg ccgcctgctg    2580
ggcatctgcc tcacctccac cgtgcagctc atcacgcagc tcatgccctt cggctgcctc    2640
ctggactatg tccgggaaca caaagacaat attggctccc agtacctgct caactggtgt    2700
gtgcagatcg caaagggcat gaactacttg gaggaccgtc gcttggtgca ccgcgacctg    2760
gcagccagga acgtactggt gaaaacaccg cagcatgtca agatcacaga ttttgggctg    2820
gccaaactgc tgggtgcgga agagaaagaa taccatgcag aaggaggcaa agtgcctatc    2880
aagtggatgg cattggaatc aatttttaca cagaatctata cccaccagag tgatgtctgg    2940
agctacgggg tgaccgtttg ggagttgatg acctttggat ccaagccata tgacggaatc    3000
cctgccagca gatctcctc catcctggag aaaggagaac gctccctca gccacccata     3060 tgtaccatcg atgtctacat gatcatggtc aagtgctgga tgatagacgc agatagtcgc    3120
```

```
ccaaagttcc gtgagttgat catcgaattc tccaaaatgg cccgagaccc ccagcgctac    3180
cttgtcattc agggggatga aagaatgcat ttgccaagtc ctacagactc caacttctac    3240
cgtgccctga tggatgaaga agacatggac gacgtggtgg atgccgacga gtacctcatc    3300
ccacagcagg gcttcttcag cagcccctcc acgtcacgga ctcccctcct gagctctctg    3360
agtgcaacca gcaacaattc caccgtggct tgcattgata gaaatgggct gcaaagctgt    3420
cccatcaagg aagacagctt cttgcagcga tacagctcag accccacagg cgccttgact    3480
gaggacagca tagacgacac cttcctccca gtgcctgaat acataaacca gtccgttccc    3540
aaaaggcccg ctggctctgt gcagaatcct gtctatcaca atcagcctct gaaccccgcg    3600
cccagcagag acccacacta ccaggacccc cacagcactg cagtgggcaa ccccgagtat    3660
ctcaacactg tccagcccac ctgtgtcaac agcacattcg acagccctgc ccactgggcc    3720
cagaaaggca gccaccaaat tagcctggac aaccctgact accagcagga cttctttccc    3780
aaggaagcca agccaaatgg catctttaag ggctccacag ctgaaaatgc agaataccta    3840
agggtcgcgc cacaaagcag tgaatttatt ggagcatgac cacggaggat agtatgagcc    3900
ctaaaaatcc agactctttc gatacccagg accaagccac agcaggtcct ccatcccaac    3960
agccatgccc gcattagctc ttagacccac agactggttt tgcaacgttt acaccgacta    4020
gccaggaagt acttccacct cgggcacatt ttgggaagtt gcattccttt gtcttcaaac    4080
tgtgaagcat ttacagaaac gcatccagca agaatattgt ccctttgagc agaaatttat    4140
cttttcaaaga ggtatatttg aaaaaaaaaa aagtatatg tgaggatttt tattgattgg    4200
ggatcttgga gtttttcatt gtcgctattg attttacttt caatgggctc ttccaacaag    4260
gaagaagctt gctggtagca cttgctaccc tgagttcatc caggcccaac tgtgagcaag    4320
gagcacaagc cacaagtctt ccagaggatg cttgattcca gtggttctgc ttcaaggctt    4380
ccactgcaaa acactaaaga tccaagaagg ccttcatggc cccagcaggc cggatcggta    4440
ctgtatcaag tcatggcagg tacagtagga taagccactc tgtcccttcc tgggcaaaga    4500
agaaacggag gggatggaat tcttccttag acttactttt gtaaaaatgt ccccacggta    4560
cttactcccc actgatggac cagtggtttc cagtcatgag cgttagactg acttgtttgt    4620
cttccattcc attgttttga aactcagtat gctgcccctg tcttgctgtc atgaaatcag    4680
caagagagga tgacacatca aataataact cggattccag cccacattgg attcatcagc    4740
atttggacca atagcccaca gctgagaatg tggaatacct aaggatagca ccgcttttgt    4800
tctcgcaaaa acgtatctcc taatttgagg ctcagatgaa atgcatcagg tcctttgggg    4860
catagatcag aagactacaa aaatgaagct gctctgaaat ctcctttagc catcaccca    4920
accccccaaa attagtttgt gttacttatg gaagatagtt ttctcctttt acttcacttc    4980
aaaagctttt tactcaaaga gtatatgttc cctccaggtc agctgccccc aaaccccctc    5040
cttacgcttt gtcacacaaa aagtgtctct gccttgagtc atctattcaa gcacttacag    5100
ctctggccac aacagggcat tttacaggtg cgaatgacga tagcattatg agtagtgtgg    5160
aattcaggta gtaaatatga aactagggtt tgaaattgat aatgctttca caacatttgc    5220
agatgtttta gaaggaaaaa agttccttcc taaaataatt tctctacaat tggaagattg    5280
gaagattcag ctagttagga gcccacccttt tttcctaatc tgtgtgtgcc ctgtaacctg    5340
actggttaac agcagtcctt tgtaaacagt gttttaaact ctcctagtca atatccaccc    5400
catccaattt atcaaggaag aaatggttca gaaaatattt tcagcctaca gttatgttca    5460
gtcacacaca catacaaaat gttccttttg cttttaaagt aattttttgac tcccagatca    5520
```

-continued

```
gtcagagccc ctacagcatt gttaagaaag tatttgattt ttgtctcaat gaaaataaaa    5580
ctatattcat ttccactcta aaaaaaaaaa aaaaaa                              5616
```

<210> SEQ ID NO 5
<211> LENGTH: 24
<212> TYPE: DNA
<213> ORGANISM: Artificial
<220> FEATURE:
<223> OTHER INFORMATION: Primer

<400> SEQUENCE: 5

```
aggtgatttt ggtctagcta cagt                                              24
```

<210> SEQ ID NO 6
<211> LENGTH: 24
<212> TYPE: DNA
<213> ORGANISM: Artificial
<220> FEATURE:
<223> OTHER INFORMATION: Primer

<400> SEQUENCE: 6

```
aggtgatttt ggtctagcta caga                                              24
```

<210> SEQ ID NO 7
<211> LENGTH: 25
<212> TYPE: DNA
<213> ORGANISM: Artificial
<220> FEATURE:
<223> OTHER INFORMATION: Primer

<400> SEQUENCE: 7

```
tagtaactca gcagcatctc agggc                                             25
```

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8

```
gaagccacac tgacgtgcct                                                   20
```

<210> SEQ ID NO 9
<211> LENGTH: 20
<212> TYPE: DNA
<213> ORGANISM: Artificial
<220> FEATURE:
<223> OTHER INFORMATION: Primer

<400> SEQUENCE: 9

```
gccgaagggc atgagctgtg                                                   20
```

<210> SEQ ID NO 10
<211> LENGTH: 22
<212> TYPE: DNA
<213> ORGANISM: Artificial
<220> FEATURE:
<223> OTHER INFORMATION: Primer

<400> SEQUENCE: 10

```
accatgcgaa gccacactga cg                                                22
```

<210> SEQ ID NO 11
<211> LENGTH: 20
<212> TYPE: DNA
<213> ORGANISM: Artificial
<220> FEATURE:
<223> OTHER INFORMATION: Primer

<400> SEQUENCE: 11
gccgaagggc atgagctgga                                                  20

<210> SEQ ID NO 12
<211> LENGTH: 22
<212> TYPE: DNA
<213> ORGANISM: Artificial
<220> FEATURE:
<223> OTHER INFORMATION: Primer

<400> SEQUENCE: 12
gtaacatcca cccagatcac tg                                               22

<210> SEQ ID NO 13
<211> LENGTH: 22
<212> TYPE: DNA
<213> ORGANISM: Artificial
<220> FEATURE:
<223> OTHER INFORMATION: Primer

<400> SEQUENCE: 13
gtgtcaagaa actagtgctg gg                                               22

<210> SEQ ID NO 14
<211> LENGTH: 22
<212> TYPE: DNA
<213> ORGANISM: Artificial
<220> FEATURE:
<223> OTHER INFORMATION: Primer

<400> SEQUENCE: 14
cccgtcgcta tcaaggaatt aa                                               22

<210> SEQ ID NO 15
<211> LENGTH: 26
<212> TYPE: DNA
<213> ORGANISM: Artificial
<220> FEATURE:
<223> OTHER INFORMATION: Primer

<400> SEQUENCE: 15
gttggctttc ggagatgttt tgatag                                           26

<210> SEQ ID NO 16
<211> LENGTH: 22
<212> TYPE: DNA
<213> ORGANISM: Artificial
<220> FEATURE:
<223> OTHER INFORMATION: Primer

<400> SEQUENCE: 16
cctcacagca gggtcttctc tg                                               22

<210> SEQ ID NO 17
<211> LENGTH: 21
<212> TYPE: DNA
<213> ORGANISM: Artificial
<220> FEATURE:
<223> OTHER INFORMATION: Primer

```
<400> SEQUENCE: 17
tggctgacct aaagccacct c                                              21
```

USE OF DNA IN CIRCULATING EXOSOMES AS A DIAGNOSTIC MARKER FOR METASTATIC DISEASE

This application is a national stage application under 35 U.S.C. 371 from PCT Application No. PCT/US2013/055395, filed Aug. 16, 2013, which claims the priority benefit of U.S. Provisional Patent Application Ser. Nos. 61/684,224, filed Aug. 17, 2012, and 61/794,384, filed Mar. 15, 2013, which are hereby incorporated by reference in their entirety.

This invention was made with government support under CA087637 awarded by the National Institutes of Health. The government has certain rights in the invention.

FIELD OF THE INVENTION

The present invention relates to methods and compositions for diagnosing, prognosing, and monitoring cancer in a subject.

BACKGROUND OF THE INVENTION

The identification of cancer biomarkers suitable for the early detection, diagnosis, prognosis, and monitoring of cancer holds great promise to improve the clinical outcome of patients by facilitating a personalized approach to treatment. At present, biomarkers (proteins, peptides, lipids, RNAs, and DNA) for conditions and diseases, such as cancer, rely almost exclusively on obtaining samples from tissue to identify the condition or disease. Methods to obtain these tissues of interest for analysis are often invasive, costly and can pose complication risks for the patient. Furthermore, use of bodily fluids to isolate or detect biomarkers often significantly dilutes a biomarker resulting in readouts that lack requisite sensitivity. Additionally, most biomarkers are produced in low or moderate amounts in normal tissues other than the diseased tissue and thus this lack of specificity can also be problematic. Despite considerable effort directed at early detection, few reliable and cost-effective screening tests have been developed that can detect, diagnose, prognose, or monitor cancer at an early stage.

The present invention is directed to overcoming these and other deficiencies in the art.

SUMMARY OF THE INVENTION

A first aspect of the present invention is directed to a method for detecting one or more BRAF and/or epidermal growth factor receptor (EGFR) mutations in a subject. This method involves isolating a sample containing exosomal DNA from the subject, and contacting the exosomal DNA from the sample with one or more reagents suitable to detect presence or absence of one or more mutations in BRAF and/or EGFR. The one or more mutations in BRAF and/or EGFR are detected based on the contacting.

Another aspect of the present invention is directed to method of prognosing cancer in a subject. This method involves selecting a subject having cancer, and obtaining, from the selected subject, a sample containing exosomal DNA. The method further involves contacting the exosomal DNA from the sample with one or more reagents suitable to detect presence or absence of one or more mutations in BRAF and/or EGFR that are associated with the cancer, and prognosing the subject based on said contacting.

Another aspect of the present invention is directed to a method of diagnosing cancer in a subject. This method involves selecting a subject having cancer, and obtaining, from the selected subject, a sample containing cancer cell-derived exosomal DNA. The method further involves detecting in the exosomal DNA from the sample, the presence or absence of one or more mutations in BRAF and/or EGFR that are associated with the cancer, and diagnosing the subject based on said contacting.

Another aspect of the present invention is directed to a method of monitoring cancer progression in a subject that involves obtaining first and second samples containing exosomal DNA, at different points in time, from the subject having cancer. The exosomal DNA in the sample is contacted with one or more reagents suitable for detecting the presence or absence of one or more mutations in BRAF and/or EGFR, and the presence or absence of the one or more mutations in BRAF and/or EGFR is detected. The method further involves comparing the presence or absence of the one or more mutations detected in the first exosomal DNA sample to the presence or absence of the one or more mutations detected in the second sample, and monitoring cancer progression in the subject based on the comparison.

Another aspect of the present invention is directed to a method of identifying a primary tumor of unknown origin in a subject having metastatic cancer. This method involves obtaining, from the subject having metastatic cancer, a sample containing exosomal DNA, and contacting the exosomal DNA from the sample with one or more reagents suitable to detect presence or absence of one or more mutations in BRAF and/or EGFR. The presence or absence of one or more mutations in BRAF and/or EGFR in the exosomal DNA of the sample are detected based on the contacting and the primary tumor of unknown origin is identified based on the detection of one or more BRAF and/or EGFR mutations.

Another aspect of the present invention is directed to a method of treating a subject having cancer. This method involves obtaining, from the subject, a sample containing exosomal DNA, and detecting in the exosomal DNA from the sample, the presence or absence of one or more mutations in BRAF and/or EGFR associated with the cancer. The method further involves selecting a suitable cancer therapeutic based on the detecting, and administering the selected cancer therapeutic to the subject having cancer.

Another aspect of the present invention is directed to a method of assessing a subject's response to treatment with a BRAF inhibitor. This method involves obtaining first and second samples containing exosomal DNA, at different points in time, from a subject being treated with a BRAF inhibitor. The first and second samples containing exosomal DNA are contacted with one or more reagents suitable for detecting the presence or absence of one or more mutations in BRAF, and the presence or absence of the one or more mutations in BRAF is detected. The presence or absence of the one or more mutations detected in the first exosomal DNA sample is compared to the presence or the absence of the one or more mutations detected in the second sample, and the subject's response to BRAF inhibitor treatment is assessed based on this comparison.

Another aspect of the present invention is directed to a method of assessing a subject's response to treatment with an EGFR inhibitor. This method involves obtaining first and second samples containing exosomal DNA, at different points in time, from a subject being treated with an EGFR inhibitor. The first and second samples containing exosomal DNA are contacted with one or more reagents suitable for detecting the presence or absence of one or more mutations in EGFR, and the presence or absence of the one or more mutations in EGFR is detected. The presence or absence of the one or more mutations detected in the first exosomal DNA sample is compared to the presence or the absence of the one or more mutations detected in the second sample, and the subject's response to EGFR inhibitor treatment is assessed based on this comparison.

Another aspect of the present invention is directed to a method of determining the metastatic potential of a cancer in a subject. This method involves obtaining a sample containing cancer cell-derived exosomes from the subject, and measuring the concentration of cancer cell-derived exosomal DNA in the sample. The concentration of cancer cell-derived exosomal DNA in the sample from the subject is compared to the concentration of exosomal DNA in a reference exosomal sample, and the metastatic potential of the cancer in the subject is determined based on the comparison.

The present invention is based on the inventors' discovery that circulating tumor exosomes contain DNA that phenocopies the mutational status of primary tumors and metastatic tumors. Accordingly, tumor derived exosomal DNA can serve as a non-invasive, diagnostic and prognostic tool by facilitating the rapid genotyping of cancers to enable early detection and optimized treatment of disease. Importantly, diagnoses and prognoses are rendered feasible using this technique in cases where a biopsy is difficult to obtain (due to inaccessibility) or when a patient has multiple sites of disease. Moreover, this tool allows for frequent monitoring of the dynamics of tumor progression and molecular changes during treatment. In addition to prognostic and diagnostic utility, the molecular information gathered from exosomal DNA analysis can be used to guide and develop personalized therapeutic regimes. Finally, because exosomes are secreted from tumors constitutively, and isolation of exosomes requires no special equipment, exosome DNA-based testing can be readily employed in all standard laboratories.

BRIEF DESCRIPTION OF THE DRAWINGS

FIG. 1A is a graph depicting the abundance of exosomal DNA ("exoDNA") derived from different types of cancer cells. FIG. 1B is a circular view of the readings of fragments along each chromosome in the whole genome sequencing analysis of exoDNA isolated from murine melanoma B16-F10 cell-derived exosomes. FIG. 1C is a graph showing the levels of exoDNA isolated from healthy human primary dermal fibroblasts ("DF") and endothelial cells ("097").

FIG. 3A shows S1 nuclease digestion of genomic DNA ("gDNA") and exoDNA derived from B16-F10 cells, indicating that exoDNA is predominantly single-stranded. FIG. 3B shows size distribution profiles of exoDNA from cultured cells. FIG. 3C is a dot blot analysis of the methylation status of exoDNA and genomic DNA using anti-5'-mecytosine antibody. Probing of the same blot using anti-DNA antibody serves as loading control.

DETAILED DESCRIPTION OF THE INVENTION

Figures 1A, 1B, 1C:
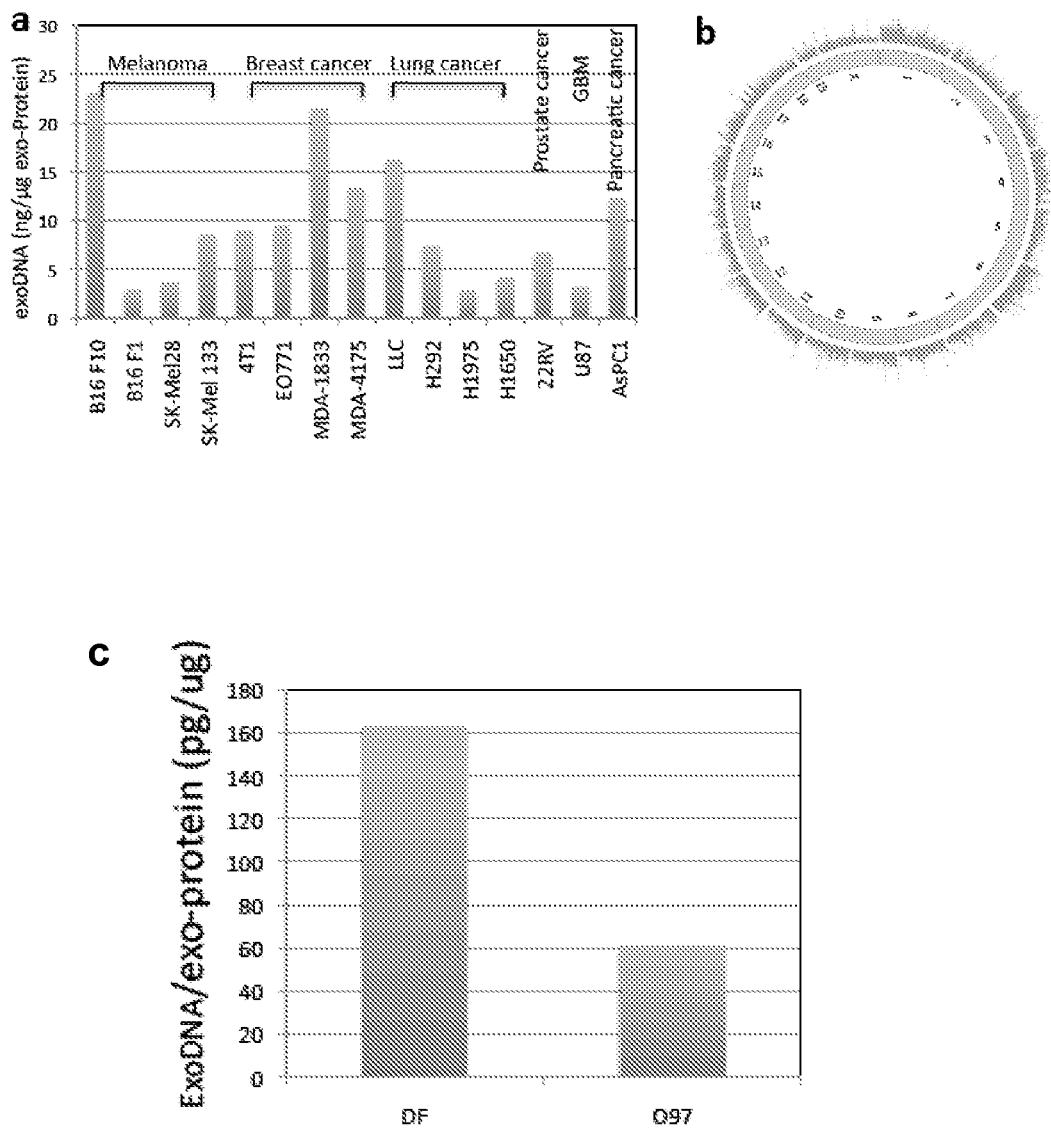
FIGS. 1A-1C show that tumor-derived exosomes contain DNA that is representative of the genotype of corresponding parent tumor cells.

The present invention is directed to methods for detecting one or more BRAF and/or epidermal growth factor receptor (EGFR) mutations in a subject. These methods involve isolating a sample containing exosomal DNA from the subject, and contacting the exosomal DNA from the sample with one or more reagents suitable to detect presence or absence of one or more mutations in BRAF and/or EGFR genes. The one or more mutations in BRAF and/or EGFR are detected based on the contacting.

One aspect of the present invention is directed to a method of detecting the one or more BRAF and/or EGFR mutations to diagnose or prognose cancer in a subject. This method involves selecting a subject having cancer, and obtaining, from the selected subject, a sample containing cancer or tumor cell-derived exosomal DNA. The method further involves contacting the cancer or tumor cell-derived exosomal DNA from the sample with one or more reagents suitable to detect presence or absence of one or more mutations in BRAF and/or EGFR associated with the cancer diagnosis or prognosis, and diagnosing or prognosing the subject based on the contacting.

Cancer diagnosis as described herein refers to determining or classifying the nature of the cancer state, e.g., the mutational or genetic phenotype of a cancer or tumor, the clinical stage of a cancer associated with its progression, and/or the metastatic nature of the cancer. Cancer diagnosis based on genetic phenotyping can help guide proper therapeutic intervention as described herein. For example, a subject diagnosed as having melanoma or brain cancer positive for a BRAF mutation is a candidate for treatment with a BRAF inhibitor. Likewise, a subject diagnosed as having lung cancer or other cancer positive for an EGFR mutation is a candidate for treatment with an EGFR inhibitor.

Cancer prognosis as described herein includes determining the probable progression and course of the cancerous condition, and determining the chances of recovery and survival of a subject with the cancer, e.g., a favorable prognosis indicates an increased probability of recovery and/or survival for the cancer patient, while an unfavorable prognosis indicates a decreased probability of recovery and/or survival for the cancer patient. A subject's prognosis can be determined by the availability of a suitable treatment (i.e., a treatment that will increase the probability of recovery and survival of the subject with cancer). For example, if the subject has a cancer, such as melanoma or brain cancer that is positive for one or more BRAF mutations as described herein, the subject has a favorable prognosis because he/she is a candidate for treatment with BRAF inhibitor therapy. Likewise, if the subject has lung cancer or other cancer that is positive for one or more EGFR mutations as described herein, the subject has a favorable prognosis because he/she is a candidate for treatment with an EGFR inhibitor therapy. Accordingly, this aspect of the present invention may further include selecting a suitable cancer therapeutic based on the determined prognosis and administering the selected therapeutic to the subject.

Prognosis also encompasses the metastatic potential of a cancer. For example, a favorable prognosis based on the presence or absence of a genetic phenotype can indicate that the cancer is a type of cancer having low metastatic potential, and the patient has an increased probability of long term recovery and/or survival. Alternatively, an unfavorable prognosis, based on the presence or absence of a genetic phenotype can indicate that the cancer is a type of cancer having a high metastatic potential, and the patient has a decreased probability of long term recovery and/or survival.

Another aspect of the present invention is directed to a method of monitoring cancer progression in a subject that involves obtaining first and second samples containing exosomal DNA, at different points in time, from the subject having cancer. The exosomal DNA in the samples is contacted with one or more reagents suitable for detecting the presence or absence of one or more mutations in BRAF and/or EGFR, and the presence or absence of the one or more mutations in BRAF and/or EGFR is detected. The method further involves comparing the presence or absence of the one or more mutations detected in the first exosomal DNA sample to the presence or absence of the one or more mutations detected in the second sample and monitoring cancer progression in the subject based on the comparison.

A change in the mutational status of BRAF and/or EGFR, for example, detecting the presence of a BRAF and/or EGFR mutation in the second exosomal DNA sample whereas no BRAF and/or EGFR mutation was detected in the first exosomal DNA sample, indicates that a change in the cancer phenotype has occurred with disease progression. This change may have therapeutic implications, i.e., it may signal the need to change the subject's course of treatment. The change can also be indicative of the progression of the cancer to a metastatic phenotype. Therefore, periodic monitoring of exosomal DNA mutational status provides a means for detecting primary tumor progression, metastasis, and facilitating optimal targeted or personalized treatment of the cancerous condition.

The time between obtaining a first exosomal sample and a second, or any additional subsequent exosomal samples can be any desired period of time, for example, weeks, months, years, as determined is suitable by a physician and based on the characteristics of the primary tumor (tumor type, stage, location, etc.). In one embodiment of this aspect of the present invention, the first sample is obtained before treatment and the second sample is obtained after treatment. Alternatively, both samples can be obtained after one or more treatments; the second sample obtained at some point in time later than the first sample.

Another aspect of the present invention is directed to a method of identifying a primary tumor of unknown origin in a subject having metastatic cancer. This method involves obtaining, from the subject having metastatic cancer, a sample containing exosomal DNA, and contacting the exosomal DNA from the sample with one or more reagents suitable to detect presence or absence of one or more mutations in BRAF and/or EGFR. The presence or absence of one or more mutations in BRAF and/or EGFR in the exosomal DNA sample are detected based on the contacting and the primary tumor of unknown origin is identified based on the detection of one or more BRAF and/or EGFR mutations.

In accordance with this aspect of the present invention, the detection of one or more BRAF mutations in a metastatic tumor or cancer cell-derived exosomal sample indicates that the primary tumor or cancer was melanoma or a form of brain cancer, e.g., glioblastoma. The detection of one or more EGFR mutations in a metastatic tumor or cancer cell derived exosomal DNA indicates that the primary tumor originated in the lung, or alternatively the primary cancer was head and neck cancer, ovarian cancer, cervical cancer, bladder cancer, or esophageal cancer.

In accordance with this aspect of the present invention, the subject may have any type of metastatic cancer, including, without limitation, metastatic melanoma, metastatic breast cancer, metastatic brain cancer, metastatic pancreatic cancer, metastatic ovarian cancer, metastatic colorectal cancer, metastatic prostate cancer, metastatic lung cancer, metastatic liver cancer, metastatic bladder cancer, metastatic bone cancer, metastatic renal cancer, and metastatic pediatric cancers.

Another aspect of the present invention is directed to a method of treating a subject having cancer. This method involves obtaining, from the subject, a sample containing exosomal DNA, and detecting in the exosomal DNA from the sample, the presence or absence of one or more mutations in BRAF and/or EGFR associated with the cancer. The method further involves selecting a suitable cancer therapeutic based on the detecting, and administering the selected cancer therapeutic to the subject having cancer.

In accordance with all aspects of the present invention, a "subject" or "patient" encompasses any animal, but preferably a mammal, e.g., human, non-human primate, a dog, a cat, a horse, a cow, or a rodent. More preferably, the subject or patient is a human. In some embodiments of the present invention, the subject has cancer, for example and without limitation, melanoma, breast cancer, brain cancer, pancreatic cancer, gastrointestinal cancer, ovarian cancer, cervical cancer, colorectal cancer, liver cancer, renal cancer, prostate cancer, lung cancer, bladder cancer, head and neck cancer, or esophageal cancer. In some embodiments, the cancer is a primary tumor, while in other embodiments, the cancer is a secondary or metastatic tumor.

In one embodiment of the present invention, the selected subject has melanoma or brain cancer (e.g., glioblastoma, ganglioblastoma, astrocytoma) and the presence or absence of a mutation in BRAF is detected in an exosomal DNA sample from the subject. BRAF is a serine/threonine protein kinase that is encoded on chromosome 7q34. The amino acid sequence and nucleotide sequence of human BRAF are provided below as SEQ ID NO: 1 and SEQ ID NO: 2, respectively.

```
Human BRAF
                                                                SEQ ID NO: 1
    Met Ala Ala Leu Ser Gly Gly Gly Gly Gly Ala Glu Pro Gly Gln
    1               5                   10                  15

Ala Leu Phe Asn Gly Asp Met Glu Pro Glu Ala Gly Ala Gly Ala
                    20                  25                  30

Ala Ala Ala Ser Ser Ala Ala Asp Pro Ala Ile Pro Glu Glu Val Trp
                    35                  40                  45

Asn Ile Lys Gln Met Ile Lys Leu Thr Gln Glu His Ile Glu Ala Leu
        50                  55                  60

Leu Asp Lys Phe Gly Gly Glu His Asn Pro Pro Ser Ile Tyr Leu Glu
    65                  70                  75                  80

Ala Tyr Glu Glu Tyr Thr Ser Lys Leu Asp Ala Leu Gln Gln Arg Glu
                        85                  90                  95

Gln Gln Leu Leu Glu Ser Leu Gly Asn Gly Thr Asp Phe Ser Val Ser
                    100                 105                 110

Ser Ser Ala Ser Met Asp Thr Val Thr Ser Ser Ser Ser Ser Ser Leu
                115                 120                 125

Ser Val Leu Pro Ser Ser Leu Ser Val Phe Gln Asn Pro Thr Asp Val
        130                 135                 140

Ala Arg Ser Asn Pro Lys Ser Pro Gln Lys Pro Ile Val Arg Val Phe
    145                 150                 155                 160

Leu Pro Asn Lys Gln Arg Thr Val Val Pro Ala Arg Cys Gly Val Thr
                        165                 170                 175

Val Arg Asp Ser Leu Lys Lys Ala Leu Met Met Arg Gly Leu Ile Pro
                    180                 185                 190

Glu Cys Cys Ala Val Tyr Arg Ile Gln Asp Gly Glu Lys Lys Pro Ile
                195                 200                 205

Gly Trp Asp Thr Asp Ile Ser Trp Leu Thr Gly Glu Glu Leu His Val
        210                 215                 220

Glu Val Leu Glu Asn Val Pro Leu Thr Thr His Asn Phe Val Arg Lys
    225                 230                 235                 240

Thr Phe Phe Thr Leu Ala Phe Cys Asp Phe Cys Arg Lys Leu Leu Phe
                        245                 250                 255

Gln Gly Phe Arg Cys Gln Thr Cys Gly Tyr Lys Phe His Gln Arg Cys
                    260                 265                 270

Ser Thr Glu Val Pro Leu Met Cys Val Asn Tyr Asp Gln Leu Asp Leu
                275                 280                 285

Leu Phe Val Ser Lys Phe Phe Glu His His Pro Ile Pro Gln Glu Glu
        290                 295                 300

Ala Ser Leu Ala Glu Thr Ala Leu Thr Ser Gly Ser Ser Pro Ser Ala
    305                 310                 315                 320

Pro Ala Ser Asp Ser Ile Gly Pro Gln Ile Leu Thr Ser Pro Ser Pro
                        325                 330                 335
```

-continued

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
        355                 360                 365

Val His Ile Asn Thr Ile Glu Pro Val Asn Ile Asp Asp Leu Ile Arg
    370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
            420                 425                 430

Glu Asp Arg Asn Arg Met Lys Thr Leu Gly Arg Arg Asp Ser Ser Asp
        435                 440                 445

Asp Trp Glu Ile Pro Asp Gly Gln Ile Thr Val Gly Gln Arg Ile Gly
    450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
            500                 505                 510

Ile Leu Leu Phe Met Gly Tyr Ser Thr Lys Pro Gln Leu Ala Ile Val
        515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Asp Phe Gly Leu Ala Thr Val Lys Ser Arg Trp Ser Gly Ser His
        595                 600                 605

Gln Phe Glu Gln Leu Ser Gly Ser Ile Leu Trp Met Ala Pro Glu Val
    610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
            660                 665                 670

Tyr Leu Ser Pro Asp Leu Ser Lys Val Arg Ser Asn Cys Pro Lys Ala
        675                 680                 685

Met Lys Arg Leu Met Ala Glu Cys Leu Lys Lys Arg Asp Glu Arg
    690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
        755                 760                 765

-continued

Human BRAF

SEQ ID NO: 2

```
cgcctcccttcccctccccgcccgacagcggccgctcgggccccggctctcggttataa60
gatggcggcgctgagcggtgcggtggtggcggcgcggagccgggccaggctctgttcaa120
cggggacatggagcccgaggccggcgccggcgccggcgccgcggcctcttcggctgcgga180
ccctgccattccggaggaggtgtggaatatcaaacaaatgattaagttgacacaggaaca240
tatagaggccctattggacaaatttggtgggagcataatccaccatcaatatatctgga300
ggcctatgaagaatacaccagcaagctagatgcactccaaaagagaaacaacagttatt360
ggaatctctggggaacggaactgattttttctgtttctagctctgcatcaatggataccgt420
tacatcttcttcctcttctagcctttcagtgctaccttcatctctttcagttttttcaaaa480
tcccacagatgtggcacggagcaaccccaagtcaccacaaaaacctatcgttagagtctt540
cctgcccaacaaacagaggacagtggtacctgcaaggtgtggagttacagtccgagacag600
tctaaagaaagcactgatgatgagaggtctaatcccagagtgctgtgctgtttacagaat660
tcaggatggagagaagaaaccaattggttgggacactgatatttcctggcttactggaga720
agaattgcatgtggaagtgttggagaatgtccacttacaacacacaacttgtacgaaa780
aacgttttcccccttagcatttttgtgacttttgtcgaaagctgcttttcccagggtttccg840
ctgtcaaacatgtggttataaatttcaccagcgttgtagtacagaagttccactgatgtg900
tgttaattataccaacttgattgctgttgtctccaagttctttgaacaccacccaat960
accacaggaagaggcgtccttagcagagactgccctaacatctggatcatcccccttccgc1020
acccgcctcggactctattggggccccaaattctcaccagtccgtctccttcaaatccat1080
tccaattccagcccttccgaccagcagatgaagatcatcgaaatcaattgggcaacg1140
agaccgatcctcatcagctccaatgtgcaatataaacacaatagaacctgtcaatattga1200
tgacttgattagagaccaaggatttcgtggtgatggaggatcaaccacagtttgtctgc1260
tacccccccctgcctcattacctggctcactaactaacgtgaaagcccttacagaaatctcc1320
aggacctcagcgagaaaggaagtcatcttcatcctcagaaacaggaatcgaatgaaaac1380
acttggtagacgggactcgagtgatgattggagattcctgatgggcagattacagtggg1440
acaaagaattggatctggatcatttggaacagtctacaagggaaagtggcatggtgatgt1500
ggcagtgaaaatgttgaatgtgacagcacctacacctcagcagttacaagccttcaaaaa1560
tgaagtaggagtactcaggaaaacacgacatgtgaatatcctactcttcatgggctattc1620
cacaaagccaaactggctattgttacccagtggtgtgaggctccagcttgtatcacca1680
tctccatatcattgagaccaaatttgagatgatcaaacttatagatattgcacgacagac1740
tgcacagggcatggattactacacgccaagtcaatcatccacagagacctcaagagtaa1800
taatatatttcttcatgaagacctcacagtaaaaataggtgattttggtctagctacagt1860
gaaatctcgatggagtgggtccccatcagttgaacagttgtctggatccattttgtggat1920
ggcaccagaagtcatcagaatgcaagataaaatccatacagctttcagtcagatgtata1980
tgcatttggaattgttctgtatgaattgatgactggacagttaccttattcaaacatcaa2040
caacagggaccagataatttttatggtgggacgaggatactgtctccagatctcagtaa2100
ggtacggagtaactgtccaaaagccatgaagagattaatgcagagtgcctcaaaaagaa2160
aagagatgagagaccactcttcccccaaattctcgcctctattgagctgctggcccgctc2220
attgccaaaaattcaccgcagtgcatcagaaccctccttgaatcgggctggtttccaaac2280
agaggattttagtctatatgcttgtgcttctccaaaaacacccatccaggcaggggata2340
tggtgcgtttcctgtccactgaaacaaatgagtgagagagttcaggagagtagcaacaaa2400
```

```
                                                   -continued
aggaaaataa atgaacatat gtttgcttat atgttaaatt gaataaaata ctctcttttt 2460
ttttaaggtg aaccaaagaa cacttgtgtg gttaaagact agatataatt tttccccaaa 2520
ctaaaattta tacttaacat tggattttta acatccaagg gttaaaatac atagacattg 2580
ctaaaaattg gcagagcctc ttctagaggc tttactttct gttccgggtt tgtatcattc 2640
acttggttat tttaagtagt aaacttcagt ttctcatgca acttttgttg ccagctatca 2700
catgtccact agggactcca gaagaagacc ctacctatgc ctgtgtttgc aggtgagaag 2760
ttggcagtcg gttagcctgg gttagataag gcaaactgaa cagatctaat ttaggaagtc 2820
agtagaattt aataattcta ttattattct taataatttt tctataacta tttctttta 2880 taacaatttg gaaaatgtgg atgtctttta tttccttgaa gcaataaact aagtttcttt 2940
ttataaaaa                                                       2949
```

BRAF activates the MAP kinase/ERK-signaling pathway, and mutations in BRAF are associated with approximately 50% of pediatric and adult malignant melanomas (Daniotti et al., "Cutaneous Melanoma in Childhood and Adolescence Shows Frequent Loss of INK4A and Gain of KIT," *J. Invest. Dermatol.* 129 (7): 1759-68 (2009), which is hereby incorporated by reference in its entirety). In addition, BRAF point mutations have been reported to occur in several low- and high-grade tumor types in pediatric and adult patients, including approximately 50-60% of gangliogliomas (MacConaill et al., "Profiling Critical Cancer Gene Mutations in Clinical Tumor Samples," *PloSOne* 4(11):e7887 (2009), and Dougherty et al. "Activating Mutations in BRAF Characterize a Spectrum of Pediatric Low-Grade Gliomas," *Neuro Oncol* 12 (7): 621-630 (2010), which are hereby incorporated by reference in their entirety), approximately 2-12% of pilocytic astrocytomas (Forshew et al., "Activation of the ERK/MAPK Pathway: A Signature Genetic Defect in Posterior Fossa Pilocytic Astrocytomas," *J Pathol.* 218:172-181 (2009); Pfister et al., "BRAF Gene Duplication Constitutes a Mechanism of MAPK Pathway Activation in Low-Grade Astrocytomas," *J Clin Invest.* 118:1739-1749 (2008); MacConaill et al., "Profiling Critical Cancer Gene Mutations in Clinical Tumor Samples," *PloSOne* 4(11):e7887 (2009); Qaddoumi et al., "Paediatric Low-Grade Gliomas and the Need for New Options for Therapy," *Cancer Biol Ther.* 8:1-7 (2009); Jacob et al., "Duplication of 7q34 is Specific to Juvenile Pilocytic Astrocytomas and a Hallmark of Cerebellar and Optic Pathway Tumors," *Brit J Cancer;* 101:722-733 (2009); and Dias-Santagata et al., "BRAF V600E Mutations Are Common in Pleomorphic Xanthoastrocytoma: Diagnostic and Therapeutic Implications," *PLoS ONE* 6(3): e17948 (2011), which are hereby incorporated by reference in their entirety), and in as many as 30% of high-grade astrocytomas. Glioma accounts for 90% of malignant central nervous system (CNS) tumors in adults and 50% in the pediatric population (Central Brain Tumor Registry of the United States, 2010).

Over 90% of BRAF mutations in melanoma are at amino acid residue 600 (SEQ ID NO: 1), and over 90% of these involve a single nucleotide mutation that causes a valine→glutamic acid change (BRAF V600E: nucleotide 1799 T>A of SEQ ID NO: 2; codon GTG>GAG) (Ascierto et al., "The Role of BRAF V600 Mutation in Melanoma," *J. Translational Med.* 10:85 (2012), which is hereby incorporated by reference in its entirety). Other mutations at this same valine residue of BRAF include a lysine substitution (BRAFV600K), an arginine substitution (BRAFV600R), and an aspartic acid substitution (BRAFV600D). The detection of any one of these BRAF V600 mutations, or other known BRAF mutations (i.e., insertions, deletions, duplications, etc.) in an exosomal DNA sample from a subject has diagnostic/prognostic and therapeutic implications in accordance with the methods of the present invention.

The BRAF V600 mutations cause constitutive activation of BRAF, which leads to activation of the downstream MEK/ERK pathway, evasion of senescence and apoptosis, uncheck replicative potential, angiogenesis, tissue invasion, metastasis, as well as evasion of immune response (Maurer et al., "Raf Kinases in Cancer-Roles and Therapeutic Opportunities," *Oncogene* 30: 3477-3488 (2011), which is hereby incorporated by reference in its entirety). Melanoma patients and patients having brain cancer identified as having a BRAF V600 mutation or other BRAF activating mutations are candidates for treatment with a BRAF inhibitor, such as vemurafenib (PLX/RG7204/RO5185426) (Sosman et al., "Survival in BRAF V600-Mutant Advanced Melanoma Treated with Vemurafenib," *N Engl J Med* 366:707-14 (2012) and Chapman et al., "Improved Survival with Vemurafenib in Melanoma with BRAF V600E Mutation," *N Engl J Med* 364"2507-2516 (2011), which are hereby incorporated by reference in their entirety), dabrafenib (Tafinlar; GSK2118436) (Gibney et al., "Clinical Development of Dabrafenib in BRAF mutant Melanoma and Other Malignancies" *Expert Opin Drug Metab Toxicol* 9(7):893-9 (2013), which is hereby incorporated by reference in its entirety), RAF265 (Su et al., "RAF265 Inhibits the Growth of Advanced Human Melanoma Tumors," *Clin Cancer Res* 18(8): 2184-98 (2012), which is hereby incorporated by reference in its entirety), and LGX818 (Stuart et al., "Preclinical Profile of LGX818: A Potent and Selective RAF Kinase Inhibitor," *Cancer Res* 72(8) Suppl 1 (2012), which is hereby incorporated by reference in its entirety).

Another aspect of the present invention is directed to a method of assessing a subject's response to treatment with a BRAF inhibitor. This method involves obtaining first and second samples containing exosomal DNA, at different points in time, from a subject being treated with a BRAF inhibitor. Suitable subjects being treated with a BRAF inhibitor include, without limitation, those having melanoma or brain cancer. The first and second samples containing exosomal DNA are contacted with one or more reagents suitable for detecting the presence or absence of one or more mutations in BRAF, and the presence or absence of the one or more mutations in BRAF is detected. The presence or absence of the one or more mutations detected in the first exosomal DNA sample is compared to the presence or absence of the one or more mutations detected in the second sample, and the subject's response to BRAF inhibitor treatment is assessed based on this comparison. If there is a decrease in the presence of BRAF mutations in the second exosomal DNA sample as compared to the first exosomal DNA sample, than the subject is responding to BRAF inhibitor treatment, i.e., the BRAF inhibitor is effectively killing tumor cells containing the BRAF mutation. If there is no decrease in the presence of BRAF mutations in the second exosomal DNA sample as compared to the first exosomal DNA sample, then the subject is likely not responding to the BRAF inhibitor treatment. This method may further include adjusting the subject's treatment regimen based on the assessment of the subject's responsiveness to therapy.

The time between obtaining a first exosomal sample and a second, or any additional subsequent exosomal samples can be any desired period of time, for example, weeks, months, years, as determined is suitable by a physician and based on the characteristics of the primary tumor (tumor type, stage, location, etc.). In one embodiment of the present invention, the first sample is obtained before treatment and the second sample is obtained after treatment. Alternatively, both samples can be obtained after one or more treatments; the second sample obtained at some point in time later than the first sample.

In another embodiment of the present invention, the presence of absence of one or more mutations in the epidermal growth factor receptor (EGFR) is detected. EGFR is a transmembrane glycoprotein with an extracellular ligand-binding domain and an intracellular domain possessing intrinsic tyrosine kinase activity. Upon receptor dimerization following ligand binding, the tyrosine kinase domain is activated and recruited for phosphorylation of intracellular targets that drive normal cell growth and differentiation. The amino acid sequence and nucleotide sequence of human EGFR are provided below as SEQ ID NO: 3 and SEQ ID NO: 4, respectively.

```
Human EGFR
                                                            SEQ ID NO: 3
Arg Pro Ser Gly Thr Ala Gly Ala Ala Leu Leu Ala Leu Leu Ala Ala
1               5                   10                  15

Leu Cys Pro Ala Ser Arg Ala Leu Glu Glu Lys Lys Val Cys Gln Gly
            20                  25                  30

Thr Ser Asn Lys Leu Thr Gln Leu Gly Thr Phe Glu Asp His Phe Leu
        35                  40                  45

Ser Leu Gln Arg Met Phe Asn Asn Cys Glu Val Val Leu Gly Asn Leu
    50                  55                  60

Glu Ile Thr Tyr Val Gln Arg Asn Tyr Asp Leu Ser Phe Leu Lys Thr
65                  70                  75                  80

Ile Gln Glu Val Ala Gly Tyr Val Leu Ile Ala Leu Asn Thr Val Glu
            85                  90                  95

Arg Ile Pro Leu Glu Asn Leu Gln Ile Ile Arg Gly Asn Met Tyr Tyr
            100                 105                 110

Glu Asn Ser Tyr Ala Leu Ala Val Leu Ser Asn Tyr Asp Ala Asn Lys
            115                 120                 125

Thr Gly Leu Lys Glu Leu Pro Met Arg Asn Leu Gln Glu Ile Leu His
            130                 135                 140

Gly Ala Val Arg Phe Ser Asn Asn Pro Ala Leu Cys Asn Val Glu Ser
145                 150                 155                 160

Ile Gln Trp Arg Asp Ile Val Ser Ser Asp Phe Leu Ser Asn Met Ser
                165                 170                 175

Met Asp Phe Gln Asn His Leu Gly Ser Cys Gln Lys Cys Asp Pro Ser
            180                 185                 190

Cys Pro Asn Gly Ser Cys Trp Gly Ala Gly Glu Glu Asn Cys Gln Lys
            195                 200                 205

Leu Thr Lys Ile Ile Cys Ala Gln Gln Cys Ser Gly Arg Cys Arg Gly
            210                 215                 220

Lys Ser Pro Ser Asp Cys Cys His Asn Gln Cys Ala Ala Gly Cys Thr
225                 230                 235                 240

Gly Pro Arg Glu Ser Asp Cys Leu Val Cys Arg Lys Phe Arg Asp Glu
            245                 250                 255

Ala Thr Cys Lys Asp Thr Cys Pro Pro Leu Met Leu Tyr Asn Pro Thr
            260                 265                 270

Thr Tyr Gln Met Asp Val Asn Pro Glu Gly Lys Tyr Ser Phe Gly Ala
            275                 280                 285
```

```
Thr Cys Val Lys Lys Cys Pro Arg Asn Tyr Val Thr Asp His Gly
290                 295                 300
Ser Cys Val Arg Ala Cys Gly Ala Asp Ser Tyr Glu Met Glu Glu Asp
305                 310                 315                 320
Gly Val Arg Lys Cys Lys Lys Cys Glu Gly Pro Cys Arg Lys Val Cys
                325                 330                 335
Asn Gly Ile Gly Ile Gly Glu Phe Lys Asp Ser Leu Ser Ile Asn Ala
            340                 345                 350
Thr Asn Ile Lys His Phe Lys Asn Cys Thr Ser Ile Ser Gly Asp Leu
        355                 360                 365
His Ile Leu Pro Val Ala Phe Arg Gly Asp Ser Phe Thr His Thr Pro
    370                 375                 380
Pro Leu Asp Pro Gln Glu Leu Asp Ile Leu Lys Thr Val Lys Glu Ile
385                 390                 395                 400
Thr Gly Phe Leu Leu Ile Gln Ala Trp Pro Glu Asn Arg Thr Asp Leu
                405                 410                 415
His Ala Phe Glu Asn Leu Glu Ile Ile Arg Gly Arg Thr Lys Gln His
            420                 425                 430
Gly Gln Phe Ser Leu Ala Val Val Ser Leu Asn Ile Thr Ser Leu Gly
        435                 440                 445
Leu Arg Ser Leu Lys Glu Ile Ser Asp Gly Asp Val Ile Ile Ser Gly
450                 455                 460
Asn Lys Asn Leu Cys Tyr Ala Asn Thr Ile Asn Trp Lys Lys Leu Phe
465                 470                 475                 480
Gly Thr Ser Gly Gln Lys Thr Lys Ile Ile Ser Asn Arg Gly Glu Asn
                485                 490                 495
Ser Cys Lys Ala Thr Gly Gln Val Cys His Ala Leu Cys Ser Pro Glu
            500                 505                 510
Gly Cys Trp Gly Pro Glu Pro Arg Asp Cys Val Ser Cys Arg Asn Val
        515                 520                 525
Ser Arg Gly Arg Glu Cys Val Asp Lys Cys Asn Leu Leu Glu Gly Glu
530                 535                 540
Pro Arg Glu Phe Val Glu Asn Ser Glu Cys Ile Gln Cys His Pro Glu
545                 550                 555                 560
Cys Leu Pro Gln Ala Met Asn Ile Thr Cys Thr Gly Arg Gly Pro Asp
                565                 570                 575
Asn Cys Ile Gln Cys Ala His Tyr Ile Asp Gly Pro His Cys Val Lys
            580                 585                 590
Thr Cys Pro Ala Gly Val Met Gly Glu Asn Asn Thr Leu Val Trp Lys
        595                 600                 605
Tyr Ala Asp Ala Gly His Val Cys His Leu Cys His Pro Asn Cys Thr
610                 615                 620
Tyr Gly Cys Thr Gly Pro Gly Leu Glu Gly Cys Pro Thr Asn Gly Pro
625                 630                 635                 640
Lys Ile Pro Ser Ile Ala Thr Gly Met Val Gly Ala Leu Leu Leu Leu
                645                 650                 655
Leu Val Val Ala Leu Gly Ile Gly Leu Phe Met Arg Arg Arg His Ile
            660                 665                 670
Val Arg Lys Arg Thr Leu Arg Arg Leu Leu Gln Glu Arg Glu Leu Val
        675                 680                 685
Glu Pro Leu Thr Pro Ser Gly Glu Ala Pro Asn Gln Ala Leu Leu Arg
690                 695                 700
Ile Leu Lys Glu Thr Glu Phe Lys Lys Ile Lys Val Leu Gly Ser Gly
705                 710                 715                 720
```

-continued

```
Ala Phe Gly Thr Val Tyr Lys Gly Leu Trp Ile Pro Glu Gly Glu Lys
                725                 730                 735

Val Lys Ile Pro Val Ala Ile Lys Glu Leu Arg Glu Ala Thr Ser Pro
            740                 745                 750

Lys Ala Asn Lys Glu Ile Leu Asp Glu Ala Tyr Val Met Ala Ser Val
        755                 760                 765

Asp Asn Pro His Val Cys Arg Leu Leu Gly Ile Cys Leu Thr Ser Thr
    770                 775                 780

Val Gln Leu Ile Thr Gln Leu Met Pro Phe Gly Cys Leu Leu Asp Tyr
785                 790                 795                 800

Val Arg Glu His Lys Asp Asn Ile Gly Ser Gln Tyr Leu Leu Asn Trp
                805                 810                 815

Cys Val Gln Ile Ala Lys Gly Met Asn Tyr Leu Glu Asp Arg Arg Leu
            820                 825                 830

Val His Arg Asp Leu Ala Ala Arg Asn Val Leu Val Lys Thr Pro Gln
        835                 840                 845

His Val Lys Ile Thr Asp Phe Gly Leu Ala Lys Leu Leu Gly Ala Glu
    850                 855                 860

Glu Lys Glu Tyr His Ala Glu Gly Gly Lys Val Pro Ile Lys Trp Met
865                 870                 875                 880

Ala Leu Glu Ser Ile Leu His Arg Ile Tyr Thr His Gln Ser Asp Val
                885                 890                 895

Trp Ser Tyr Gly Val Thr Val Trp Glu Leu Met Thr Phe Gly Ser Lys
            900                 905                 910

Pro Tyr Asp Gly Ile Pro Ala Ser Glu Ile Ser Ser Ile Leu Glu Lys
        915                 920                 925

Gly Glu Arg Leu Pro Gln Pro Pro Ile Cys Thr Ile Asp Val Tyr Met
    930                 935                 940

Ile Met Val Lys Cys Trp Met Ile Asp Ala Asp Ser Arg Pro Lys Phe
945                 950                 955                 960

Arg Glu Leu Ile Ile Glu Phe Ser Lys Met Ala Arg Asp Pro Gln Arg
                965                 970                 975

Tyr Leu Val Ile Gln Gly Asp Glu Arg Met His Leu Pro Ser Pro Thr
            980                 985                 990

Asp Ser Asn Phe Tyr Arg Ala Leu Met Asp Glu Glu Asp Met Asp Asp
        995                 1000                1005

Val Val Asp Ala Asp Glu Tyr Leu Ile Pro Gln Gln Gly Phe Phe
    1010                1015                1020

Ser Ser Pro Ser Thr Ser Arg Thr Pro Leu Leu Ser Ser Leu Ser
    1025                1030                1035

Ala Thr Ser Asn Asn Ser Thr Val Ala Cys Ile Asp Arg Asn Gly
    1040                1045                1050

Leu Gln Ser Cys Pro Ile Lys Glu Asp Ser Phe Leu Gln Arg Tyr
    1055                1060                1065

Ser Ser Asp Pro Thr Gly Ala Leu Thr Glu Asp Ser Ile Asp Asp
    1070                1075                1080

Thr Phe Leu Pro Val Pro Glu Tyr Ile Asn Gln Ser Val Pro Lys
    1085                1090                1095

Arg Pro Ala Gly Ser Val Gln Asn Pro Val Tyr His Asn Gln Pro
    1100                1105                1110

Leu Asn Pro Ala Pro Ser Arg Asp Pro His Tyr Gln Asp Pro His
    1115                1120                1125

Ser Thr Ala Val Gly Asn Pro Glu Tyr Leu Asn Thr Val Gln Pro
    1130                1135                1140
```

-continued

Thr Cys Val Asn Ser Thr Phe Asp Ser Pro Ala His Trp Ala Gln
     1145                1150                1155

Lys Gly Ser His Gln Ile Ser Leu Asp Asn Pro Asp Tyr Gln Gln
     1160                1165                1170

Asp Phe Phe Pro Lys Glu Ala Lys Pro Asn Gly Ile Phe Lys Gly
     1175                1180                1185

Ser Thr Ala Glu Asn Ala Glu Tyr Leu Arg Val Ala Pro Gln Ser
     1190                1195                1200

Ser Glu Phe Ile Gly Ala
     1205

Human EGFR
                                                       SEQ ID NO: 4
ccccggcgca gcgcggccgc agcagcctcc gccccccgca cggtgtgagc gcccgacgcg    60
gccgaggcgg ccggagtccc gagctagccc cggcggccgc cgccgcccag accgacgac   120
aggccacctc gtcggcgtcc gcccgagtcc ccgcctcgcc gccaacgcca caaccaccgc   180
gcacggcccc ctgactccgt ccagtattga tcgggagagc cggagcgagc tcttcgggga   240
gcagcgatgc gaccctccgg gacggccggg gcagcgctcc tggcgctgct ggctgcgctc   300
tgcccggcga gtcgggctct ggaggaaaag aaagtttgcc aaggcacgag taacaagctc   360
acgcagttgg cacttttga agatcatttt ctcagcctcc agaggatgtt caataactgt   420
gaggtggtcc ttgggaattt ggaaattacc tatgtgcaga ggaattatga tctttccttc   480
ttaaagacca tccaggaggt ggctggttat gtcctcattg ccctcaacac agtggagcga   540
attcctttgg aaaacctgca gatcatcaga ggaaatatgt actacgaaaa ttcctatgcc   600
ttagcagtct tatctaacta tgatgcaaat aaaaccggac tgaaggagct gcccatgaga   660
aatttacagg aaatcctgca tggcgccgtg cggttcagca acaaccctgc cctgtgcaac   720
gtggagagca tccagtggcg ggacatagtc agcagtgact ttctcagcaa catgtcgatg   780
gacttccaga accacctggg cagctgccaa aagtgtgatc caagctgtcc caatgggagc   840
tgctggggtg caggagagga gaactgccag aaactgacca aaatcatctg tgcccagcag   900
tgctccgggc gctgccgtgg caagtccccc agtgactgct gccacaacca gtgtgctgca   960
ggctgcacag gccccgggga gagcgactgc ctggtctgcc gcaaattccg agacgaagcc  1020
acgtgcaagg acacctgccc cccactcatg ctctacaacc ccaccacgta ccagatggat  1080
gtgaaccccg aggggaaata cagctttggt gccacctgcg tgaagaagtg tccccgtaat  1140
tatgtggtga cagatcacgg ctcgtgcgtc cgagcctgtg ggccgacag ctatgagatg  1200
gaggaagacg gcgtccgcaa gtgtaagaag tgcgaagggc cttgccgcaa agtgtgtaac  1260
ggaataggta ttggtgaatt taaagactca ctctccataa atgctacgaa tattaaacac  1320
ttcaaaaact gcacctccat cagtggcgat ctccacatcc tgccggtggc atttaggggt  1380
gactccttca cacatactcc tcctctggat ccacaggaac tggatattct gaaaaccgta  1440
aaggaaatca caggttttt gctgattcag gcttggcctg aaaacaggac ggacctccat  1500
gcctttgaga acctagaaat catacgcggc aggaccaagc aacatggtca gttttctctt  1560
gcagtcgtca gcctgaacat aacatccttg ggattacgct ccctcaagga taagtgat  1620
ggagatgtga taatttcagg aaacaaaaat ttgtgctatg caaatacaat aaactggaaa  1680
aaactgtttg gacctccgg tcagaaaacc aaaattataa gcaacagagg tgaaaacagc  1740
tgcaaggcca caggccaggt ctgccatgcc ttgtgctccc ccgagggctg ctgggccg   1800
gagcccaggg actgcgtctc ttgccggaat gtcagccgag caggggaatg cgtggacaag  1860
tgcaaccttc tggagggtga gccaagggag tttgtggaga actctgagtg catacagtgc  1920

-continued

```
cacccagagt gcctgcctca ggccatgaac atcacctgca caggacgggg accagacaac   1980
tgtatccagt gtgcccacta cattgacggc ccccactgcg tcaagacctg cccggcagga   2040
gtcatgggag aaaacaacac cctggtctgg aagtacgcag acgccggcca tgtgtgccac   2100
ctgtgccatc caaactgcac ctacggatgc actgggccag gtcttgaagg ctgtccaacg   2160
aatgggccta agatcccgtc catcgccact gggatggtgg gggccctcct cttgctgctg   2220
gtggtggccc tggggatcgg cctcttcatg cgaaggcgcc acatcgttcg gaagcgcacg   2280
ctgcggaggc tgctgcagga gagggagctt gtggagcctc ttacacccag tggagaagct   2340
cccaaccaag ctctcttgag gatcttgaag gaaactgaat tcaaaaagat caaagtgctg   2400
ggctccggtg cgttcggcac ggtgtataag ggactctgga tcccagaagg tgagaaagtt   2460
aaaattcccg tcgctatcaa ggaattaaga gaagcaacat ctccgaaagc caacaaggaa   2520
atcctcgatg aagcctacgt gatggccagc gtggacaacc cccacgtgtg ccgcctgctg   2580
ggcatctgcc tcacctccac cgtgcagctc atcacgcagc tcatgccctt cggctgcctc   2640
ctggactatg tccgggaaca caaagacaat attggctccc agtacctgct caactggtgt   2700
gtgcagatcg caaagggcat gaactacttg gaggaccgtc gcttggtgca ccgcgacctg   2760
gcagccagga acgtactggt gaaaacaccg cagcatgtca agatcacaga ttttgggctg   2820
gccaaactgc tgggtgcgga agagaaagaa taccatgcag aaggaggcaa agtgcctatc   2880
aagtggatgg cattggaatc aattttacac agaatctata cccaccagag tgatgtctgg   2940
agctacgggg tgaccgtttg ggagttgatg acctttggat ccaagccata tgacggaatc   3000
cctgccagcg agatcctctc catcctggag aaaggagaac gcctccctca gccacccata   3060
tgtaccatcg atgtctacat gatcatggtc aagtgctgga tgatagacgc agatagtcgc   3120
ccaaagttcc gtgagttgat catcgaattc tccaaaatgg cccgagaccc ccagcgctac   3180
cttgtcattc agggggatga aagaatgcat ttgccaagtc ctacagactc caacttctac   3240
cgtgccctga tggatgaaga agacatggac gacgtggtgg atgccgacga gtacctcatc   3300
ccacagcagg gcttcttcag cagcccctcc acgtcacgga ctcccctcct gagctctctg   3360
agtgcaacca gcaacaattc caccgtggct tgcattgata gaaatgggct gcaaagctgt   3420
cccatcaagg aagacagctt cttgcagcga tacagctcag accccacagg cgccttgact   3480
gaggacagca tagacgacac cttcctccca gtgcctgaat acataaacca gtccgttccc   3540
aaaaggcccg ctggctctgt gcagaatcct gtctatcaca atcagcctct gaaccccgcg   3600
cccagcagag acccacacta ccaggacccc cacagcactg cagtgggcaa ccccgagtat   3660
ctcaacactg tccagcccac ctgtgtcaac agcacattcg acagccctgc ccactgggcc   3720
cagaaaggca gccaccaaat tagcctggac aaccctgact accagcagga cttctttccc   3780
aaggaagcca agccaaatgg catctttaag ggctccacag ctgaaaatgc agaataccta   3840
agggtcgcgc cacaaagcag tgaatttatt ggagcatgac cacggaggat agtatgagcc   3900
ctaaaaatcc agactctttc gatacccagg accaagccac agcaggtcct ccatcccaac   3960
agccatgccc gcattagctc ttagacccac agactggttt tgcaacgttt acaccgacta   4020
gccaggaagt acttccacct cgggcacatt ttgggaagtt gcattccttt gtcttcaaac   4080
tgtgaagcat ttacagaaac gcatccagca agaatattgt cccttttgagc agaaatttat   4140 ctttcaaaga ggtatatttg aaaaaaaaaa aagtatatg tgaggatttt tattgattgg   4200
ggatcttgga gttttcatt gtcgctattg attttacttt caatgggctc ttccaacaag   4260
gaagaagctt gctggtagca cttgctaccc tgagttcatc caggcccaac tgtgagcaag   4320
gagcacaagc cacaagtctt ccagaggatg cttgattcca gtggttctgc ttcaaggctt   4380
```

```
                                        -continued
ccactgcaaa acactaaaga tccaagaagg ccttcatggc cccagcaggc cggatcggta      4440
ctgtatcaag tcatggcagg tacagtagga taagccactc tgtcccttcc tgggcaaaga      4500
agaaacggag gggatggaat tcttccttag acttactttt gtaaaaatgt ccccacggta      4560
cttactcccc actgatggac cagtggtttc cagtcatgag cgttagactg acttgtttgt      4620
cttccattcc attgttttga aactcagtat gctgccctg tcttgctgtc atgaaatcag       4680
caagagagga tgacacatca aataataact cggattccag cccacattgg attcatcagc      4740
atttggacca atagcccaca gctgagaatg tggaatacct aaggatagca ccgcttttgt      4800
tctcgcaaaa acgtatctcc taatttgagg ctcagatgaa atgcatcagg tcctttgggg      4860
catagatcag aagactacaa aaatgaagct gctctgaaat ctcctttagc catcacccca      4920
accccccaaa attagtttgt gttacttatg gaagatagtt ttctccttt acttcacttc       4980 aaaagctttt tactcaaaga gtatatgttc cctccaggtc agctgccccc aaaccccctc      5040
cttacgcttt gtcacacaaa aagtgtctct gccttgagtc atctattcaa gcacttacag      5100
ctctggccac aacagggcat tttacaggtg cgaatgacag tagcattatg agtagtgtgg      5160
aattcaggta gtaaatatga aactagggtt tgaaattgat aatgctttca caacatttgc      5220
agatgtttta gaaggaaaaa agttccttcc taaaataatt tctctacaat tggaagattg      5280
gaagattcag ctagttagga gcccacctt tttcctaatc tgtgtgtgcc ctgtaacctg       5340
actggttaac agcagtcctt tgtaaacagt gttttaaact ctcctagtca atatccaccc      5400
catccaattt atcaaggaag aaatggttca gaaaatattt tcagcctaca gttatgttca      5460
gtcacacaca catacaaaat gttcctttg cttttaaagt aattttttgac tcccagatca      5520 gtcagagccc ctacagcatt gttaagaaag tatttgattt ttgtctcaat gaaaataaaa      5580
ctatattcat ttccactcta aaaaaaaaaa aaaaaa                                5616
```

Several EGFR mutations leading to constitutive activation have been associated with neoplastic growth and cancer progression in a variety of cancers, including lung cancer (in particular non-small cell lung carcinoma), head and neck cancer, ovarian cancer, cervical cancer, bladder cancer, and esophageal cancer (Nicholson et al., "EGFR and Cancer Prognosis," *Eur J Cancer* 37(4):9-15 (2001), which is hereby incorporated by reference in its entirety). Therefore, subjects suitable for EGFR mutational detection in accordance with this embodiment of the present invention include subjects having any one of the aforementioned cancers.

A gain of function mutation suitable for detection in exosomal DNA samples in accordance with the present invention, includes, without limitation, the L858R mutation which results in leucine to arginine amino acid substitution at amino acid position 858 of human EGFR (SEQ ID NO: 3). This mutation occurs within the kinase domain (exon 21) and arises from a T>G nucleotide mutation at position 2573 of the EGFR gene sequence (SEQ ID NO: 4) (NCBI dbSNP reference SNP rs121434568; Mitsudomi et al., "Epidermal Growth Factor Receptor in Relation to Tumor Development: EGFR Gene and Cancer," *FEBS J* 277(2): 301-8 (2010), which are hereby incorporated by reference in their entirety).

Another gain of function mutation in EGFR suitable for detection in accordance with the present invention is the T790M mutation which results in a threonine to methionine mutation at amino acid position 790 in EGFR (SEQ ID NO: 3). This mutation occurs within the kinase domain (exon 20) and arises from a C>T mutation at nucleotide 2369 of the EGFR gene (SEQ ID NO: 4) (NCBI dbSNP reference SNP rs121434569; Tam et al., "Distinct Epidermal Growth Factor Receptor and KRAS Mutation Patterns in Non-Small Cell Lung Cancer Patients with Different Tobacco Exposure and Clinicopathologic Features," *Clin Cancer Res* 12:1647 (2006), which are hereby incorporated by reference in their entirety).

Another gain of function mutation in EGFR suitable for detection in accordance with the present invention is an in-frame deletion in exon 19. For example, deletions in amino acid residues 746-750, 746-751, 746-752, 747-751, 747-749, and 752-759 (SEQ ID NO: 3) have all been associated with lung cancer (see e.g., Mitsudomi et al., "Epidermal Growth Factor Receptor in Relation to Tumor Development: EGFR Gene and Cancer," *FEBS J* 277(2): 301-8 (2010), which is hereby incorporated by reference in its entirety). Detection of any one of these exon 19 deletions in exosomal DNA from a subject has prognostic/diagnostic and therapeutic implications in accordance with the present invention.

Subjects identified as having any of the above described EGFR mutations, or any other known EGFR mutations (i.e., insertions, deletions, duplications, etc), particularly gain-of-function mutations, are candidates for treatment using EGFR inhibitory agents which induce apoptosis and reduce proliferation of tumor growth (Ciardiello et al., "A Novel Approach in the Treatment of Cancer: Targeting the Epidermal Growth Factor Receptor," *Clin Cancer Res* 7:2958-2970 (2001); Ritter et al., "The Epidermal Growth Factor Receptor-Tyrosine Kinase: A Promising Therapeutic Target in Solid Tumors," *Semin Oncol* 30:3-11 (2003), which are hereby incorporated by reference in their entirety). Suitable EGFR inhibitors include, without limitation, small-molecule inhibitors of EGFR such as Gefitnib, Erlotinib (Tarceva), Afatinib (Gilotrif), Lapatinib (Tyverb) and monoclonal antibody inhibitors such as Panitumumab (Vectibix) and Cetuximab (Erbitux). Other EGFR inhibitors that are known in the art are also suitable for use in accordance with the methods of the present invention.

Another aspect of the present invention is directed to a method of assessing a subject's response to treatment with an EGFR inhibitor. This method involves obtaining first and second samples containing exosomal DNA, at different points in time, from a subject being treated with an EGFR inhibitor. Suitable subjects being treated with an EGFR inhibitor include, without limitation, those having lung cancer, head and neck cancer, ovarian cancer, cervical cancer, bladder cancer and esophageal cancer. The first and second samples containing exosomal DNA are contacted with one or more reagents suitable for detecting the presence or absence of one or more mutations in EGFR, and the presence or absence of the one or more mutations in EGFR is detected. The presence or absence of the one or more mutations detected in the first exosomal DNA sample is compared to the presence or absence of one or more mutations detected in the second sample, and the subject's response to EGFR inhibitor treatment is assessed based on this comparison. If there is a decrease in the presence of EGFR mutations in the second exosomal DNA sample as compared to the first exosomal DNA sample, then the subject is responding to EGFR inhibitor treatment, i.e., the EGFR inhibitor is effectively killing tumor cells containing the EGFR mutation. If there is no decrease in the presence of EGFR mutations in the second exosomal DNA sample as compared to the first exosomal DNA sample, then the subject is not responsive to the EGFR inhibitor treatment. This method may further include adjusting the subject's treatment regimen based on the assessment of the subject's responsiveness to therapy.

As noted above, the first sample can be obtained before treatment and the second sample obtained after treatment. Alternatively, both samples can be obtained after one or more treatments; the second sample obtained at some point in time later than the first sample.

Another aspect of the present invention is directed to a method of determining the metastatic potential of a cancer in a subject. This method involves obtaining a sample containing cancer cell-derived exosomes from the subject, and measuring the concentration of exosomal DNA in the sample. The concentration of exosomal DNA in the sample from the subject is compared to the concentration of exosomal DNA in a reference exosomal sample, and the metastatic potential of the cancer in the subject is determined based on the comparison.

In accordance with this aspect of the present invention, and as described herein, exosomes derived from tumors having high metastatic potential contain much higher levels of DNA than exosomes derived from tumors having a low or no metastatic potential. Therefore, in one embodiment of the present invention, the reference exosomal sample is an exosomal sample derived from tumor cells known to have low metastatic potential such as B16F1 melanoma cells, H1975 and H1650 lung cancer cells, or U87 glioblastoma cells. A higher concentration of DNA in the exosomal sample from the subject as compared to the concentration of DNA in exosomes derived from cells of low metastatic potential indicates the subject has a cancer with a high metastatic potential. If the exosomal sample from the subject has the same or lower concentration of DNA as compared to the concentration of DNA in exosomes derived from cells of low metastatic potential, then the subject has a cancer with a low metastatic potential. Alternatively, a reference exosomal sample can be derived from tumor cells having a high metastatic potential, such as B16F10 melanoma cells or Lewis lung carcinoma cells. If the exosomal sample from the subject has the same or a higher concentration of DNA as compared to exosomes derived from tumor cells of high metastatic potential, then the subject has a cancer with high metastatic potential. If the exosomal sample from the subject has a lower concentration of DNA as compared to exosomes derived from tumor cells of high metastatic potential, then the subject has a cancer with low metastatic potential "Exosomes" are microvesicles released from a variety of different cells, including cancer cells (i.e., "cancer-derived exosomes"). These small vesicles (50-100 nm in diameter) derive from large multivesicular endosomes and are secreted into the extracellular milieu. The precise mechanisms of exosome release/shedding remain unclear; however, this release is an energy-requiring phenomenon, modulated by extracellular signals. They appear to form by invagination and budding from the limiting membrane of late endosomes, resulting in vesicles that contain cytosol and that expose the extracellular domain of membrane-bound cellular proteins on their surface. Using electron microscopy, studies have shown fusion profiles of multivesicular endosomes with the plasma membrane, leading to the secretion of the internal vesicles into the extracellular environment. The rate of exosome release is significantly increased in most neoplastic cells and occurs continuously. Increased release of exosomes and their accumulation appear to be important in the malignant transformation process.

In accordance with the methods of the present invention, exosomes can be isolated or obtained from most biological fluids including, without limitation, blood, serum, plasma, ascites, cyst fluid, pleural fluid, peritoneal fluid, cerebral spinal fluid, tears, urine, saliva, sputum, nipple aspirates, lymph fluid, fluid of the respiratory, intestinal, and genitourinary trances, breast milk, intra-organ system fluid, or combinations thereof.

An enriched population of exosomes can be obtained from a biological sample using methods known in the art. For example, exosomes may be concentrated or isolated from a biological sample using size exclusion chromatography, density gradient centrifugation, differential centrifugation (Raposo et al. "B lymphocytes secrete antigen-presenting vesicles," *J Exp Med* 183(3): 1161-72 (1996), which is hereby incorporated by reference in its entirety), anion exchange and/or gel permeation chromatography (for example, as described in U.S. Pat. No. 6,899,863 to Dhellin et al., and U.S. Pat. No. 6,812,023 to Lamparski et al., which are hereby incorporated by reference in their entirety), sucrose density gradients or organelle electrophoresis (for example, as described in U.S. Pat. No. 7,198,923), magnetic activated cell sorting (MACS) (Taylor et al., "MicroRNA signatures of tumor-derived exosomes as diagnostic biomarkers of ovarian cancer" *Gynecol Oncol* 110(1): 13-21 (2008), which is hereby incorporated by reference in its entirety), nanomembrane ultrafiltration (Cheruvanky et al., "Rapid isolation of urinary exosomal biomarkers using a nanomembrane ultrafiltration concentrator," *Am J Physiol Renal Physiol* 292(5): F1657-61 (2007), which is hereby incorporated by reference in its entirety), immunoabsorbent capture, affinity purification, microfluidic separation, or combinations thereof.

Exosomes isolated from a bodily fluid can be enriched for those originating from a specific cell type, for example, lung, pancreas, stomach, intestine, bladder, kidney, ovary, testis, skin, colorectal, breast, prostate, brain, esophagus, liver, placenta, fetus cells. Because the exosomes often carry surface molecules such as antigens from their donor cells, surface molecules may be used to identify, isolate and/or enrich for exosomes from a specific donor cell type. In this way, exosomes originating from distinct cell populations can be analyzed for their nucleic acid content. For example, tumor (malignant and non-malignant) exosomes carry tumor-associated surface antigens and may be detected, isolated and/or enriched via these specific tumor-associated surface antigens. In one example, the surface antigen is epithelial-cell-adhesion-molecule (EpCAM), which is specific to exosomes from carcinomas of lung, colorectal, breast, prostate, head and neck, and hepatic origin, but not of hematological cell origin (Balzar et al. "The Biology of the 17-1A Antigen (Ep-CAM)," *J Mol Med* 77(10): 699-712 (1999); Went et al. "Frequent EpCam Protein Expression in Human Carcinomas," *Hum Pathol* 35(1): 122-8 (2004), which are hereby incorporated by reference in their entirety). In another example, the surface antigen is CD24, which is a glycoprotein specific to urine microvesicles (Keller et al. "CD24 is a Marker of Exosomes Secreted into Urine and Amniotic Fluid," *Kidney Int* 72(9): 1095-102 (2007), which is hereby incorporated by reference in its entirety). In yet another example, the surface antigen is CD70, carcinoembryonic antigen (CEA), EGFR, EGFRvIII and other variants, Fas ligand, TRAIL, tranferrin receptor, p38.5, p97 and HSP72. Alternatively, tumor specific exosomes may be characterized by the lack of surface markers, such as the lack of CD80 and CD86 expression.

The isolation of exosomes from specific cell types can be accomplished, for example, by using antibodies, aptamers, aptamer analogs or molecularly imprinted polymers specific for a desired surface antigen. In one embodiment, the surface antigen is specific for a cancer type. In another embodiment, the surface antigen is specific for a cell type which is not necessarily cancerous. One example of a method of exosome separation based on cell surface antigen is provided in U.S. Pat. No. 7,198,923, which is hereby incorporated by reference in its entirety. As described in, e.g., U.S. Pat. No. 5,840,867 to Toole and U.S. Pat. No. 5,582,981 to Toole, which are hereby incorporated by reference in their entirety, aptamers and their analogs specifically bind surface molecules and can be used as a separation tool for retrieving cell type-specific exosomes. Molecularly imprinted polymers also specifically recognize surface molecules as described in, e.g., U.S. Pat. Nos. 6,525,154, 7,332,553 and 7,384,589, which are hereby incorporated by reference in their entirety, and are a tool for retrieving and isolating cell type-specific exosomes.

The exosomal fraction from a bodily fluid of a subject can be pre-treated with DNase to eliminate or substantially eliminate any DNA located on the surface or outside of the exosomes. Without DNAse pre-treatment, short DNA fragments on the outside of the exosomes may remain and co-isolate with nucleic acids extracted from inside the exosomes. Thus, elimination of all or substantially all DNA associated with the outside or surface of the exosomes by pre-treatment of with DNase, has the ability to enrich for internal exosomal nucleic acids (i.e., DNA or RNA).

It may be beneficial or otherwise desirable to extract DNA or RNA from the exosomes prior to or for analysis. In accordance with all aspects of the present invention, analysis of BRAF and/or EGFR mutations can be carried out using exosomal DNA or RNA. In some embodiments of the present invention, it is desirable only to analyze single-stranded exosomal DNA. DNA and RNA molecules can be isolated from an exosome and the concentration of each (i.e., total DNA or total RNA) quantified using any number of procedures, which are well-known in the art, the particular extraction procedure chosen based on the particular biological sample. For example, methods for extracting nucleic acids from urinary exosomes are described in Miranda et al. "Nucleic Acids within Urinary Exosomes/Microvesicles are Potential Biomarkers for Renal Disease," *Kidney Int*. 78:191-9 (2010) and in PCT/US10/042,365 to Russo, which are hereby incorporated by reference in their entirety. In some instances, with some techniques, it may also be possible to analyze the nucleic acid without extraction from the exosome.

In one embodiment, the extracted nucleic acids, including DNA and/or RNA, are analyzed directly without an amplification step. Direct analysis may be performed with different methods including, but not limited to, nanostring technology. NanoString technology enables identification and quantification of individual target molecules in a biological sample by attaching a color coded fluorescent reporter to each target molecule. This approach is similar to the concept of measuring inventory by scanning barcodes. Reporters can be made with hundreds or even thousands of different codes allowing for highly multiplexed analysis. The technology is described in a publication by Geiss et al. "Direct Multiplexed Measurement of Gene Expression with Color-Coded Probe Pairs," *Nat Biotechnol* 26(3): 317-25 (2008), which is hereby incorporated by reference in its entirety.

In another embodiment, it may be beneficial or otherwise desirable to amplify the nucleic acid of the exosome prior to analyzing it. Methods of nucleic acid amplification are commonly used and generally known in the art. If desired, the amplification can be performed such that it is quantitative. Quantitative amplification will allow quantitative determination of relative amounts of the various exosomal nucleic acids.

In one embodiment, the extracted nucleic acid is DNA. In another embodiment, the extracted nucleic acid is RNA. RNAs are preferably reverse-transcribed into complementary DNAs. Such reverse transcription may be performed alone or in combination with an amplification step, e.g., using reverse transcription polymerase chain reaction (RT-PCR), which may be further modified to be quantitative, e.g., quantitative RT-PCR as described in U.S. Pat. No. 5,639,606, which is hereby incorporated by reference in its entirety.

Nucleic acid amplification methods include, without limitation, polymerase chain reaction (PCR) (U.S. Pat. No. 5,219,727, which is hereby incorporated by reference in its entirety) and its variants such as in situ polymerase chain reaction (U.S. Pat. No. 5,538,871, which is hereby incorporated by reference in its entirety), quantitative polymerase chain reaction (U.S. Pat. No. 5,219,727, which is hereby incorporated by reference in its entirety), nested polymerase chain reaction (U.S. Pat. No. 5,556,773), self sustained sequence replication and its variants (Guatelli et al. "Isothermal, In vitro Amplification of Nucleic Acids by a Multienzyme Reaction Modeled after Retroviral Replication," *Proc Natl Acad Sci USA* 87(5): 1874-8 (1990), which is hereby incorporated by reference in its entirety), transcriptional amplification system and its variants (Kwoh et al. "Transcription-based Amplification System and Detection of Amplified Human Immunodeficiency Virus type 1 with a Bead-Based Sandwich Hybridization Format," *Proc Natl Acad Sci USA* 86(4): 1173-7 (1989), which is hereby incorporated by reference in its entirety), Qb Replicase and its variants (Miele et al. "Autocatalytic Replication of a Recombinant RNA." *J Mol Biol* 171(3): 281-95 (1983), which is hereby incorporated by reference in its entirety), cold-PCR (Li et al. "Replacing PCR with COLD-PCR Enriches Variant DNA Sequences and Redefines the Sensitivity of Genetic Testing." *Nat Med* 14(5): 579-84 (2008), which is hereby incorporated by reference in its entirety) or any other nucleic acid amplification methods, followed by the detection of the amplified molecules using techniques known to those of skill in the art. Especially useful are those detection schemes designed for the detection of nucleic acid molecules if such molecules are present in very low numbers.

Detecting the presence or absence of one or more mutations in BRAF and/or EGFR genes in a tumor or cancer cell-derived exosomal DNA sample from a subject can be carried out using methods that are well known in the art.

In one embodiment of the present invention, the one or more mutations in the one or more identified genes is detected using a hybridization assay. In a hybridization assay, the presence or absence of a gene mutation is determined based on the hybridization of one or more allele-specific oligonucleotide probes to one or more nucleic acid molecules in the exosomal DNA sample from the subject. The oligonucleotide probe or probes comprise a nucleotide sequence that is complementary to at least the region of the gene that contains the mutation of interest. The oligonucleotide probes are designed to be complementary to the wildtype, non-mutant nucleotide sequence and/or the mutant nucleotide sequence of the one or more genes to effectuate the detection of the presence or the absence of the mutation in the sample from the subject upon contacting the sample with the oligonucleotide probes. A variety of hybridization assays that are known in the art are suitable for use in the methods of the present invention. These methods include, without limitation, direct hybridization assays, such as northern blot or Southern blot (see e.g., Ausabel et al., Current Protocols in Molecular Biology, John Wiley & Sons, NY (1991)). Alternatively, direct hybridization can be carried out using an array based method where a series of oligonucleotide probes designed to be complementary to a particular non-mutant or mutant gene region are affixed to a solid support (glass, silicon, nylon membranes). A labeled DNA or cDNA sample from the subject is contacted with the array containing the oligonucleotide probes, and hybridization of nucleic acid molecules from the sample to their complementary oligonucleotide probes on the array surface is detected. Examples of direct hybridization array platforms include, without limitation, the Affymetrix GeneChip or SNP arrays and Illumina's Bead Array. Alternatively sample is bound to a solid support (often DNA or PCR amplified DNA) and labeled with oligonucleotides in solution (either allele specific or short so as to allow sequencing by hybridization).

Other common genotyping methods include, but are not limited to, restriction fragment length polymorphism assays; amplification based assays such as molecular beacon assays, nucleic acid arrays, high resolution melting curve analysis (Reed and Wittwer, "Sensitivity and Specificity of Single-Nucleotide Polymorphism Scanning by High Resolution Melting Analysis," *Clinical Chem* 50(10): 1748-54 (2004), which is hereby incorporated by reference in its entirety); allele-specific PCR (Gaudet et al., "Allele-Specific PCR in SNP Genotyping," *Methods Mol Biol* 578: 415-24 (2009), which is hereby incorporated by reference in its entirety); primer extension assays, such as allele-specific primer extension (e.g., Illumina® Infinium® assay), arrayed primer extension (see Krjutskov et al., "Development of a Single Tube 640-plex Genotyping Method for Detection of Nucleic Acid Variations on Microarrays," *Nucleic Acids Res.* 36(12) e75 (2008), which is hereby incorporated by reference in its entirety), homogeneous primer extension assays, primer extension with detection by mass spectrometry (e.g., Sequenom® iPT EX SNP genotyping assay) (see Zheng et al., "Cumulative Association of Five Genetic Variants with Prostate Cancer," *N. Eng. J. Med.* 358(9):910-919 (2008), which is hereby incorporated by reference in its entirety), multiplex primer extension sorted on genetic arrays; flap endonuclease assays (e.g., the Invader® assay) (see Olivier M., "The Invader Assay for SNP Genotyping," *Mutat. Res.* 573 (1-2) 103-10 (2005), which is hereby incorporated by reference in its entirety); 5' nuclease assays, such as the TaqMan® assay (see U.S. Pat. No. 5,210,015 to Gelfand et al. and U.S. Pat. No. 5,538,848 to Livak et al., which are hereby incorporated by reference in their entirety); and oligonucleotide ligation assays, such as ligation with rolling circle amplification, homogeneous ligation, OLA (see U.S. Pat. No. 4,988,617 to Landgren et al., which is hereby incorporated by reference in its entirety), multiplex ligation reactions followed by PCR, wherein zipcodes are incorporated into ligation reaction probes, and amplified PCR products are determined by electrophoretic or universal zipcode array readout (see U.S. Pat. Nos. 7,429,453 and 7,312,039 to Barany et al., which are hereby incorporated by reference in their entirety). Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection. In general, the methods for analyzing genetic aberrations are reported in numerous publications, not limited to those cited herein, and are available to those skilled in the art. The appropriate method of analysis will depend upon the specific goals of the analysis, the condition/history of the patient, and the specific cancer(s), diseases or other medical conditions to be detected, monitored or treated.

Alternatively, the presence or absence of one or more mutations identified supra can be detected by direct sequencing of the genes, or preferably particular gene regions comprising the one or more identified mutations, from the patient sample. Direct sequencing assays typically involve isolating DNA sample from the subject using any suitable method known in the art, and cloning the region of interest to be sequenced into a suitable vector for amplification by growth in a host cell (e.g. bacteria) or direct amplification by PCR or other amplification assay. Following amplification, the DNA can be sequenced using any suitable method. As preferable sequencing method involves high-throughput next generation sequencing (NGS) to identify genetic variation. Various NGS sequencing chemistries are available and suitable for use in carrying out the claimed invention, including pyrosequencing (Roche® 454), sequencing by reversible dye terminators (Illumina® HiSeq, Genome Analyzer and MiSeq systems), sequencing by sequential ligation of oligonucleotide probes (Life Technologies® SOLiD), and hydrogen ion semiconductor sequencing (Life Technologies®, Ion Torrent™). Alternatively, classic sequencing methods, such as the Sanger chain termination method or Maxam-Gilbert sequencing, which are well known to those of skill in the art, can be used to carry out the methods of the present invention.

EXAMPLES

The examples below are intended to exemplify the practice of the present invention but are by no means intended to limit the scope thereof.

Materials and Methods for Examples 1-4

Exosomes were prepared using differential ultracentrifugation methods. Cells were cultured under standard condition for 2-3 days and the conditioned medium was harvested and subjected to 500 g and 20,000 g centrifugation for 10 min and 20 min, respectively to get rid of dead cells, cell debris, and large particles. Exosomes were pelleted down by ultracentrifugation at 100,000 g for 70 min, followed by washing with PBS once. The exosomes were resuspended in PBS for downstream analysis.

For plasma samples, the plasma was filtered through a 1.2 µm membrane to remove debris and large particles, then subjected to ultracentrifugation to pellet and wash exosomes. DNA was extracted from exosomes using QIAamp DNA mini kit (QIAGEN) following manufacturer's protocol and eluted with 50 µl of 10 mM Tris pH8.0. DNA quality and quantity were analyzed using Nanodrop and Agilent Bioanalyzer RNA chip.

For detecting mutations using allele-specific PCR, standard PCR reactions were conducted using primers (Table 1) that can distinguish wild type alleles versus the mutant allele, and the PCR product was analyzed by agarose gel electrophoresis.

High resolution melting curve analysis (HRM) analysis was performed using primers spanning the mutations and High Resolution Melting Master mix (Roche) and the real time PCR and analysis were conducted using Light Cycler 480 (Roche).

TABLE 1

Primers used in AS-PCR and HRM Analyses

| | | SEQ ID NO: |
|---|---|---|
| BRAF AS-PCR Primers | | |
| V allele forward primer | AGGTGATTTTGGTCTAGCTACAGT | 5 |
| E allele forward primer | AGGTGATTTTGGTCTAGCTACAGA | 6 |
| Common reverse primer | TAGTAACTCAGCAG CATCTCAGGGC | 7 |
| EGFR T790M AS-PCR primers: | | |
| T allele forward primer | gaagccacactgacgtgcct | 8 |
| T allele reverse primer | gccgaagggcatgagctgTg | 9 |
| M allele forward primer | accatgcgaagccacactgacg | 10 |
| M allele reverse primer | gccgaagggcatgagctgGa | 11 |
| EGFR exon 19 deletion AS-PCR (multiplex) primers | | |
| Multiplex Primer 1 | GTAACATCCACCCAGATCACTG | 12 |
| Multiplex Primer 2 | GTGTCAAGAAACTAGTGCTGGG | 13 |
| Multiplex Primer 3 | CCCGTCGCTATCAAGGAATTAA | 14 |
| Multiplex Primer 4 | GTTGGCTTTCGGAGATGTTTTGATAG | 15 |
| EGFR L858 HRM Primers | | |
| Forward primer | CCTCACAGCAGGGTCTTCTCTG | 16 |
| Reverse primer | TGGCTGACCTAAAGCCACCTC | 17 |

Example 1

Characterization of Tumor Cell Derived Exosomal DNA

Exosomes are small membrane vesicles (30-100 nm) of endocytotic origin which are secreted by most cell types and are crucial for intercellular communication in various biological processes including tumorigenesis and metastatic progression. Tumor cell-derived exosomes can be detected in patients' plasma, and the molecules selectively packaged within these particles, such as miRNAs and proteins represent potential diagnostic and prognostic biomarkers for guiding therapeutic decisions. Recently, DNA has been associated with exosomes derived from cell lines. However, whether the association of DNA with exosomes is a general feature of exosomes, especially those derived from tumor cells, or whether exoDNA has potential as a diagnostic biomarker, has not been previously investigated.

To address these questions the abundance of DNA associated with exosomes isolated from a variety of murine and human tumor derived cell lines was examined (FIG. 1A). This analysis revealed that DNA is associated with exosomes derived from all tumor cells examined, including melanoma (B16-F10, B16-F1, A375P, and A375M), breast cancer (EO771, 4T1, 67NR, DB7, MBMDA-MB-231, MDA-1833, and MDA-4175), pancreatic cancer (AsPC1 and PANC1), glioblastoma multiforme (U87), and prostate cancer (22RV1). These results indicate that the presence of exoDNA is a general feature of different types of cancer cells. Interestingly, exosomes from tumor derived cell lines with high metastatic potential (e.g. melanoma and pancreatic) appeared to have higher levels of exoDNA than those with low metastatic potential, indicating that the relative abundance of exoDNA may serve as an indicator of the metastatic potential of cancer cells. Whether DNA is present in exosomes derived from normal stromal cells, such as fibroblasts, was also examined. Although exoDNA could be isolated from exosomes derived from fibroblasts (human primary dermal fibroblasts, fibroblast isolated from mammary tissue), the level was ~20-fold less than that derived from tumor cells (FIG. 1C). Therefore, the abundance of exoDNA varies by cell type and cell of origin, with tumor cell exosomes containing considerably more DNA than healthy cell exosomes.

Figure 2:
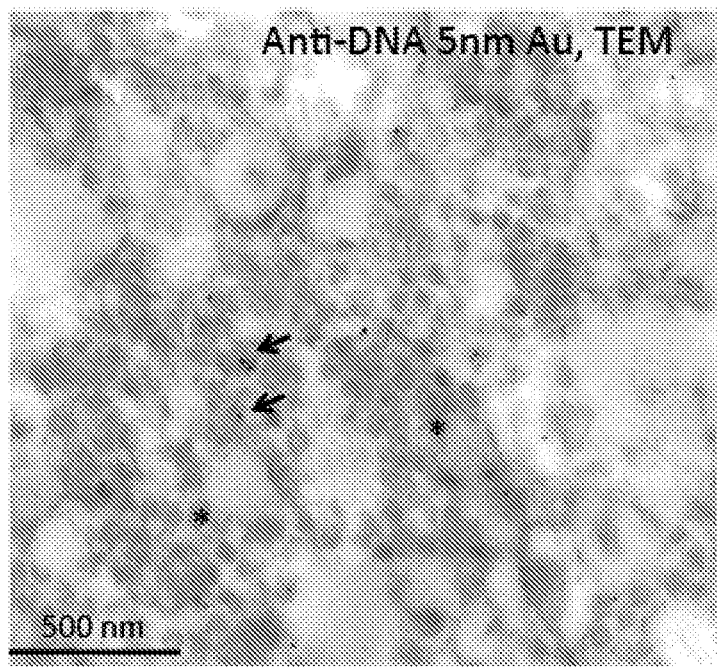
FIG. 2 is an immunogold electron microscopy image of exosomes derived from B16-F10 cells using an anti-DNA antibody.
Figures 3A, 3B, 3C:
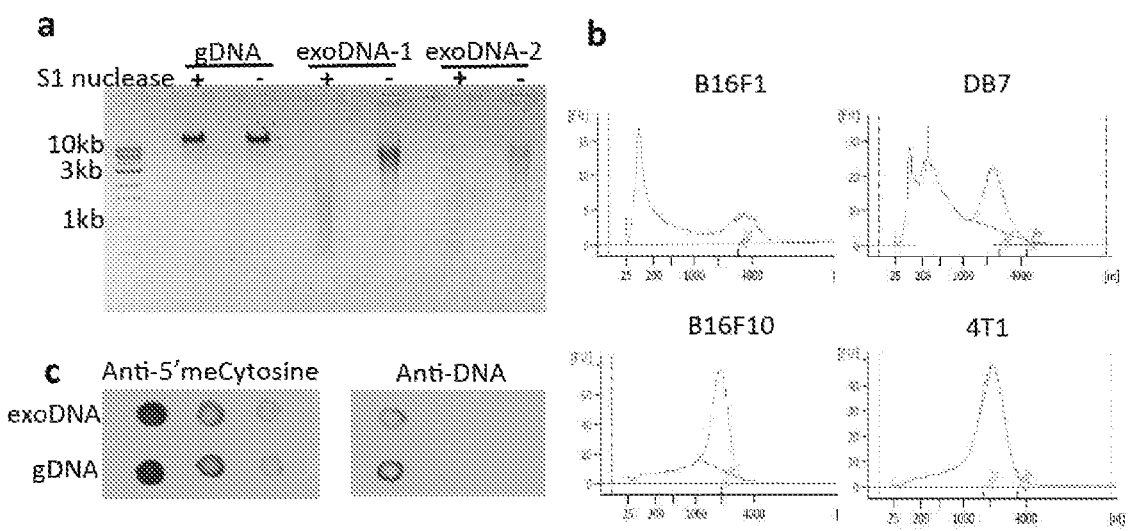
FIGS. 3A-3C depict the characterization of exoDNA.

DNA-immunogold electron microscopy of exosomes from the B16-F10 murine melanoma model showed that ~10% of the exosomes contained DNA (FIG. 2). Further analysis revealed that exoDNA is predominantly single-stranded, as demonstrated by its sensitivity to S1 nuclease digestion (FIG. 3A), consistent with previous findings reported by Balaj et al., "Tumour Microvesicles Contain Retrotransposon Elements and Amplified Oncogene Sequences," *Nature Communications* 2:180 (2011), which is hereby incorporated by reference in its entirety. The size distribution profiles of exoDNA from plasma were examined using Agilent Bioanalyzer RNA chips (FIG. 3B). The majority of the exoDNA isolated from the highly metastatic B16-F10 and 4T1 cell lines centered around 2000 nucleotides (nt). In contrast, the size distribution of exoDNA from poorly metastatic cell lines (B16-F1 and DB7) was predominantly in the 100-200 nt range with a much smaller contribution in the 2000 nt range. This finding reflects that exoDNA biogenesis varies by cell type with longer fragments observed in the exosomes from more malignant tumors as compared to those with lower malignant potential.

The methylation status of exoDNA was also examined. 5'-cytosine methylation is a major modification of DNA involved in various biological processes, such as transcription and DNA repair. As shown in the dot blot analysis of FIG. 3C, exoDNA is methylated to a level similar to that of genomic DNA.

Figure 3D:
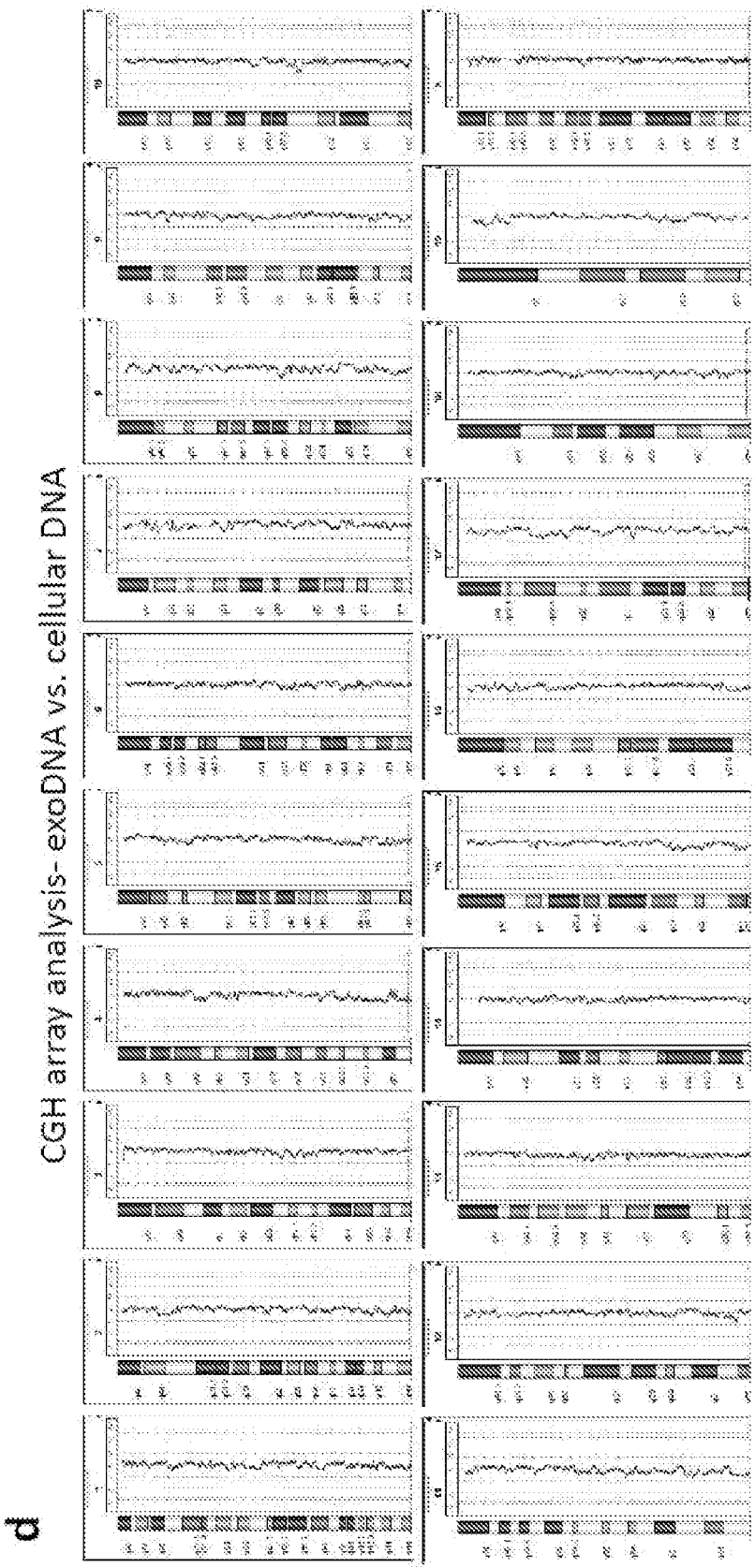
FIG. 3D shows the results of a comparative genomic hybridization (CGH) array analysis comparing exoDNA and gDNA derived from the B16-F10 cell.

Both high throughput whole genome sequencing (FIG. 1B) and comparative genomic hybridization array analyses (FIG. 3D) were carried out to determine the nature of exoDNA. These analyses revealed that whole genomic DNA (but not mitochondrial DNA) was represented in exoDNA. No bias for gene-coding versus intergenic regions and sense versus antisense strands of genecoding regions was observed in the exoDNA. In addition, no specific fragments were highly enriched or depleted in the exoDNA pool compared to the genomic DNA.

Example 2

Mutational Analysis of Tumor Cell Line Derived Exosomal DNA

Figure 4:
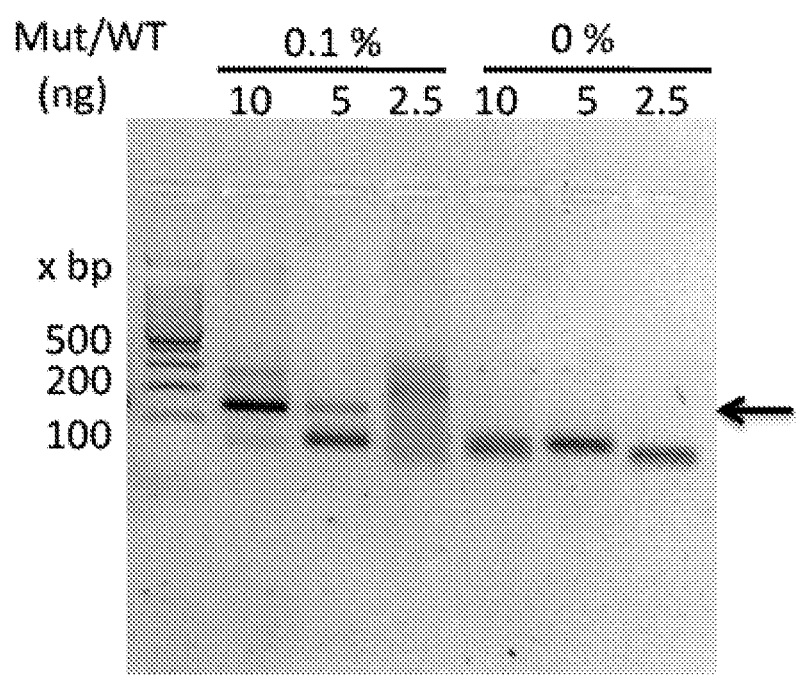
FIG. 4 shows the sensitivity and specificity of allele-specific polymerase chain reaction (AS-PCR) for detecting the BRAF(V600E) mutation. Genomic DNA samples containing no BRAF(V600E) mutation or 0.1% of this mutation were used as template for AS-PCR to assess the sensitivity and specificity of the assay. Different amounts of template DNA (as low as 2.5 ng) were examined. The results indicate that the assay can detect the presence of mutation in as low as 5 ng of template containing 0.1% mutation without false positive identification of the mutation.

The finding that exoDNA represents genomic DNA prompted the determination of whether exoDNA could be utilized as a surrogate for tumor tissues or cells to detect tumor-associated genetic mutations. To this end, exoDNA isolated from cell line derived exosomes of various cancers, including melanoma and lung cancer was examined. The BRAF(V600E) mutation is present in ~50% of malignant melanomas. Allele-specific polymerase chain reaction (AS-PCR) analysis was performed to evaluate the mutational status of BRAF in exoDNA isolated from several human primary melanoma cell lines which harbor either wild type (WT; SK-Mel146 and SK-Mel 147) or mutated BRAF (SK-Mel 28, SK-Mel 133, SK-Mel 192, and SK-Mel 267) (Jarry et al., "Real-time Allele-specific Amplification for Sensitive Detection of the BRAF Mutation V600E," *Mol. Cell. Probes* 18: 349-52 (2004), which is hereby incorporated by reference in its entirety). Genomic DNA containing no BRAF(V600E) mutation or 0.1% of this mutation was used as template for AS-PCR to assess the sensitivity and specificity of the assay. Different amount of template DNA (as low as 2.5 ng) was examined. The results indicate that the assay can detect the presence of mutation in as low as 5 ng of template with 0.1% mutation without false positive identification of the mutation (FIG. 4).

Figures 5A, 5B, 5C:
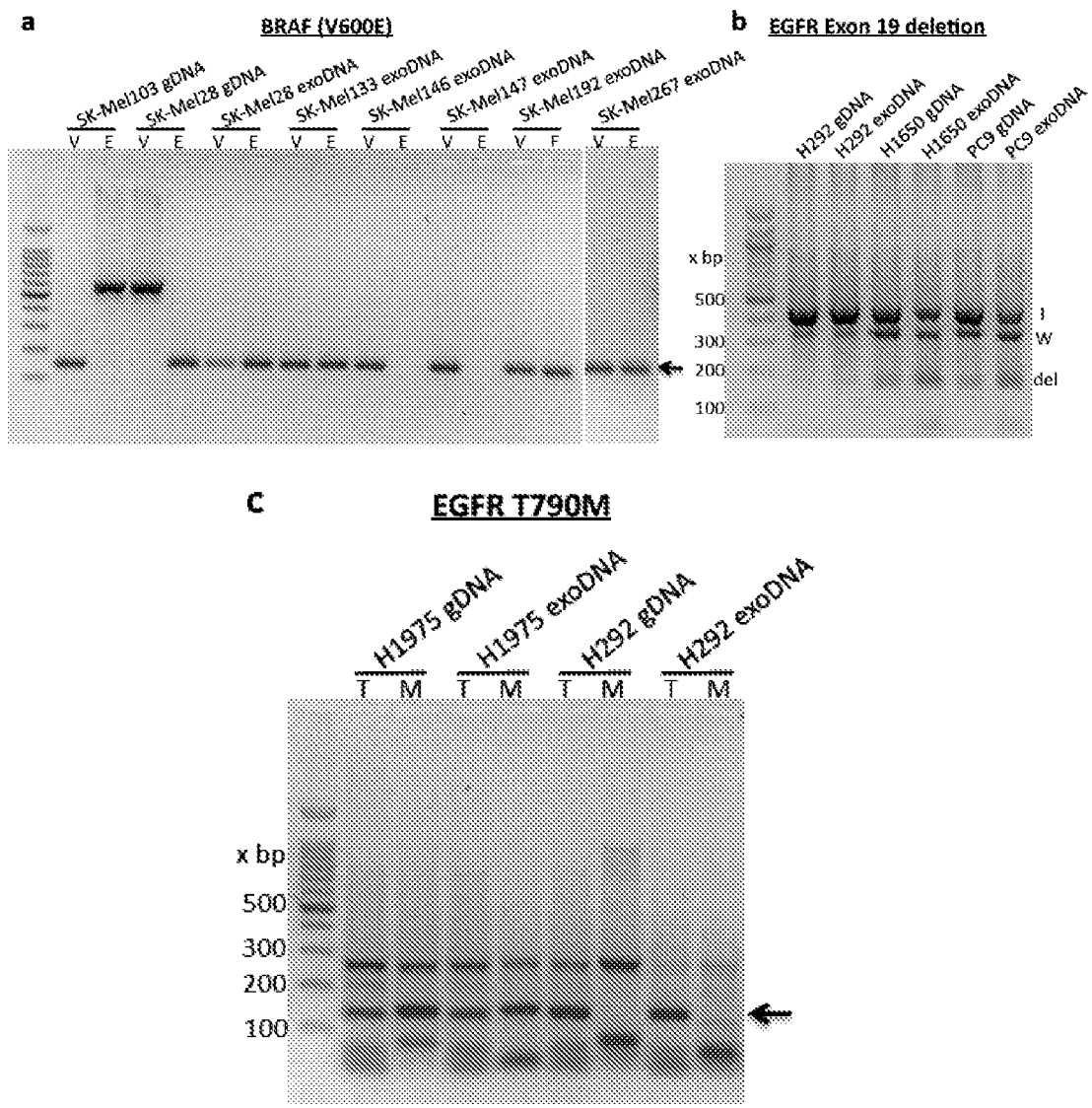
FIGS. 5A-5D show the detection of genetic mutations in exoDNA isolated from cultured tumor cells. The mutational status for BRAF and EGFR was examined using exoDNA derived from cell lines originated from melanoma and non-small cell lung carcinoma ("NSCLC"), respectively. AS-PCR was used for detection of the BRAF(V600E) mutation in melanoma cell lines as shown in FIG. 5A ("V" represents wildtype (WT) allele; "E" represents mutant allele); the EGFR exon 19 deletion in NSCLC cell lines as shown in FIG. 5B ("I" represents internal control for both wildtype and mutant alleles; "W" represents wildtype allele; "del" represents deletion of amino acid residues 746-750 of Exon 19), and the T790M mutation in NSCLC cell lines as shown in FIG. 5C ("T" represents wildtype allele; "M" represents mutant allele). High Resolution Melt ("FIRM") analysis was used for detecting the EGFR L858R mutation in NSCLC cells (FIG. 5D). The existence of a point mutation results in distinct melting curve of the amplicon that spans the mutation from that of the wildtype amplicon, and identical melting curves of amplicons originated from gDNA and exoDNA indicate their identical genotypes.

Using primers that distinguished between wildtype ("V") and mutant alleles ("E") of BRAF, the mutant allele was detected in exoDNA of all cell lines containing the mutation, whereas only the wildtype allele was detected in those cell lines with non-mutated BRAF (FIG. 5A). These findings demonstrated that exoDNA reflects the mutational BRAF status of the parental cell lines.

Figure 5D:
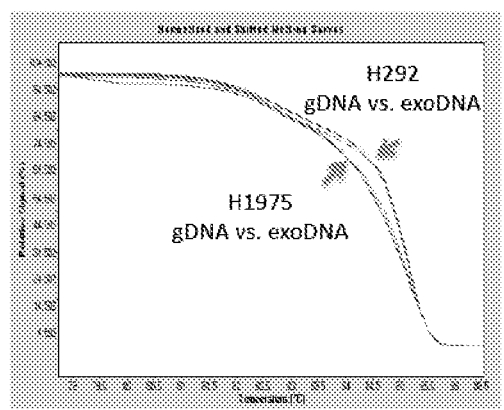

A second example of a well-described tumor-associated mutation is the epidermal growth factor receptor (EGFR), which is mutated in several types of cancers, including non-small cell lung cancer (NSCLC). Gain of function mutations within the kinase domain of EGFR, such as the L858R point mutation, a deletion in 19 exon (19Del), and the T790M gate-keeper mutation, are crucial for selecting those patients who will benefit from targeted therapy using tyrosine kinase inhibitors. Here, AS-PCR and high resolution melting curve analysis (HRM) were utilized to assess exosomal DNA from several NSCLC cell lines, including the H292 cell line (wildtype), the H1975 cell line (having the L858R and T790M point mutations), and the H1650 and PC9 cell lines (having a deletion in exon 19). EGFR mutations were positively identified in exoDNA isolated from cultured NSCLC cell lines having these known EGFR mutations as shown in FIGS. 5B-5D.

Example 3

Mutational Analysis of Exosomal DNA in Animal Model of Melanoma

Figure 6:
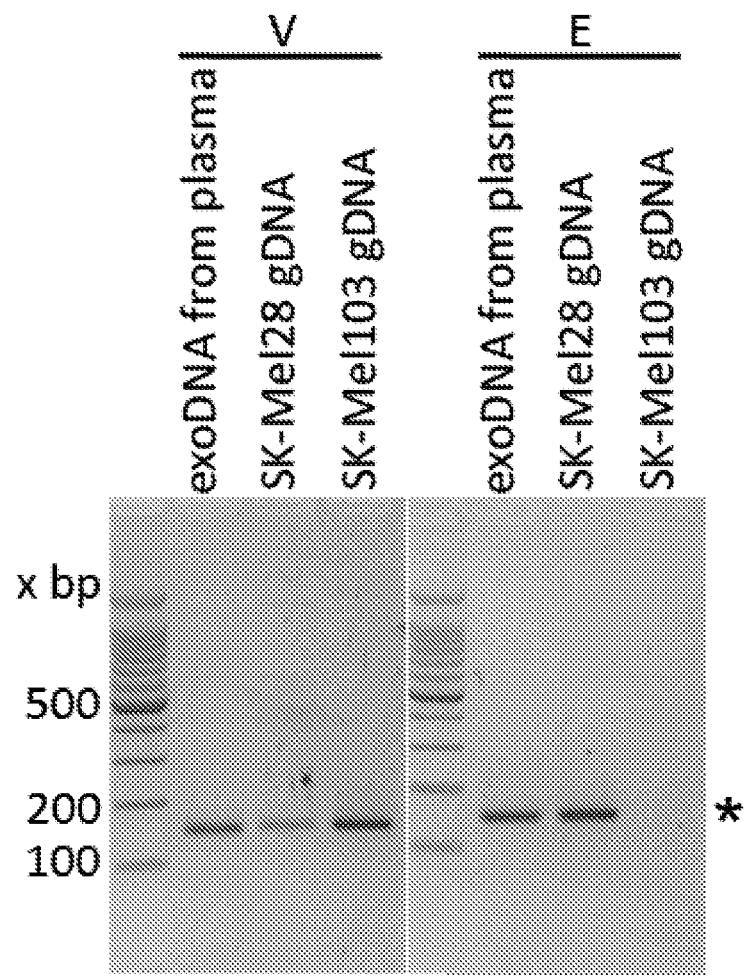
FIG. 6 shows the detection of BRAF V600E mutation in circulating exoDNA isolated from melanoma-bearing mice. Circulating exosomes were isolated from the plasma of mice bearing melanoma (subcutaneously implanted with human melanoma cell line, Sk-Mel-28). AS-PCR was employed to detect the BRAF V600E mutation in the extracted exoDNA, with gDNA isolated from Sk-Mel-28 and Sk-Mel-103 cells as positive and negative control for V600E mutation (WT (V) and mutant (E) alleles). Asterisk indicates the band of expected PCR products.

To assess the potential of detecting tumor-associated genetic mutations using circulating exoDNA, an animal model of melanoma was employed. Human melanoma cells harboring BRAF(V600E) mutation (Sk-Mel 28) were subcutaneously implanted in the flanks of NOD/SCID mice. Plasma was harvested when the tumor reached the size limit allowed by the standard animal protocol. Circulating exosomes were isolated using ultracentrifugation procedure, and DNA was extracted and assayed for the BRAF(V600E) mutation. As demonstrated in FIG. 6, the V600E mutation was readily detected in the circulating exoDNA isolated from melanoma-bearing mice ("exoDNA from plasma").

Example 4

Mutational Analysis of Exosomal DNA in Clinical Samples of Melanoma

Figure 7:
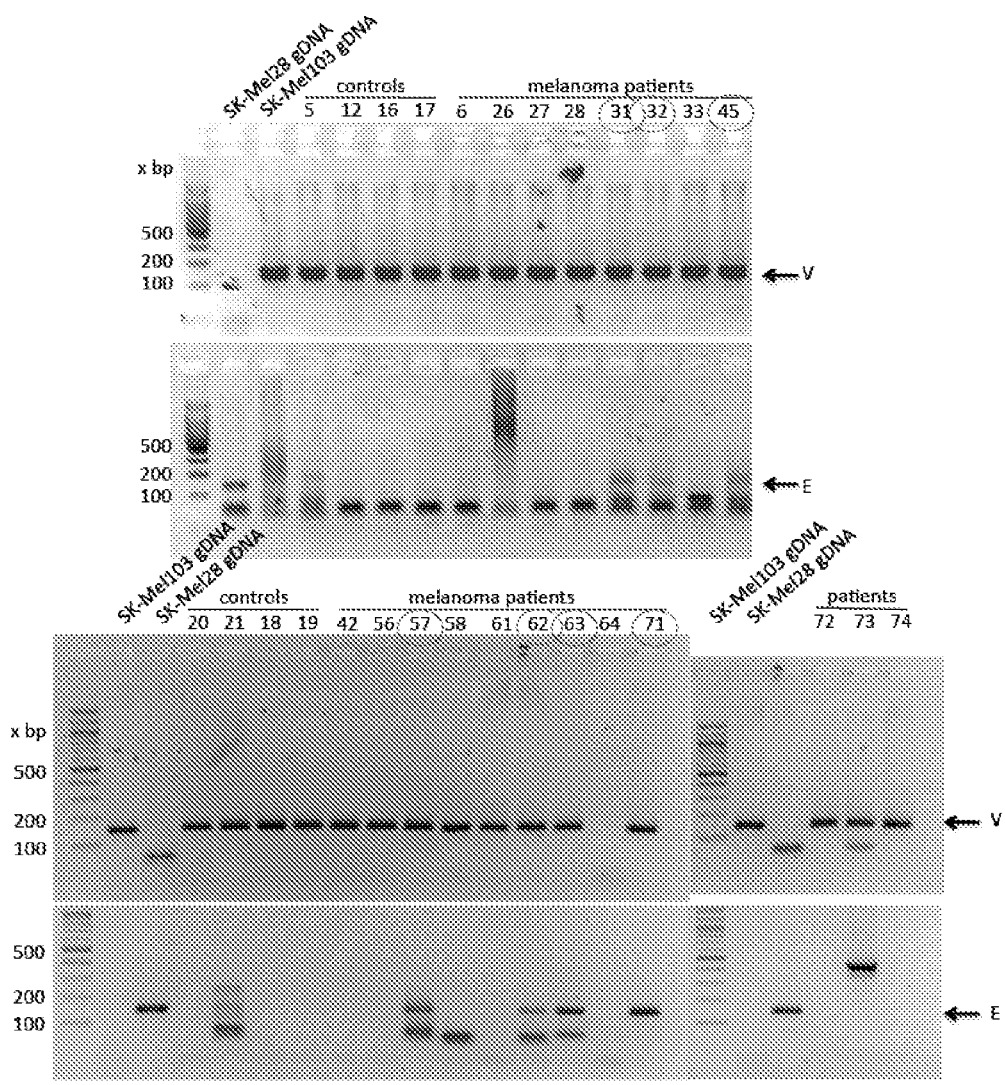
FIG. 7 shows AS-PCR analysis of exoDNA isolated from the plasma of patients with melanoma or healthy subjects for determination of BRAF(V600E) mutation. Genomic DNA isolated from Sk-Mel-28 and Sk-Mel-103 cells served as positive and negative controls for the V600E mutation (WT (V) and mutant (E) alleles). The BRAF mutation was detected in exoDNA of 7 of the melanoma patient samples and one of the healthy control patient samples.

Tumor-derived exosomes in patients are released into the peripheral circulation and can be isolated from a small volume of plasma. To explore the potential clinical application of exoDNA as a novel non-invasive alternative strategy to biopsies, melanoma was utilized as a model system. ExoDNA was isolated from the plasma of patients with melanoma (N=19) or healthy subjects (N=10), and AS-PCR was applied to detect the BRAF(V600E) mutation. As shown in FIG. 7, the BRAF(V600E) mutation was readily detected in ~37% (7/19) of melanoma patients (expected frequency) but in none of the healthy subjects.

In a follow-up study the BRAF(V600E) mutational status in a healthy control group (n=8) and a group of melanoma patients with disease at different stages (I-IV) (n=12) was examined. As summarized in Table 2, no BRAF V600E mutation in circulating exosomes from the healthy control subjects (n=8) was detected, indicating no false positive identification using this assay. All patients selected for this study (n=12) had their primary tumors or lymph nodes positive for metastasis and examined for BRAF mutational status, as listed in Table 2. The BRAF V600E mutation was detected in the circulating exosomes of three out of six patients who were determined to be positive for the BRAF mutation in their primary tumors, suggesting the possibility that BRAF mutational status can change during metastatic progression. In support of these findings, the BRAF V600E mutation was detected in circulating exosomes of two out of six patients who were found to be negative for the BRAF V600E mutation in their primary tumor, implicating that circulating exosomes, which are shed from not only primary tumors but also metastatic tumors, have the diagnostic/prognostic potential of revealing a more comprehensive mutational status of overall metastatic disease. Exosomes in circulation represent comprehensively the genetic information from tumors that could be potentially missed by biopsy, therefore providing higher sensitivity of mutation detection. In addition, circulating tumor-derived exosomes may reflect the patients' response to therapy and can serve as a means for monitoring dynamic changes of tumor burden in patients undergoing therapy.

TABLE 2

Examination of BRAF V600E Mutation Status in Melanoma Patient Plasma-Derived ExoDNA

|  | Tumor | exoDNA |
|---|---|---|
| Cont5 | – | – |
| Cont12 | – | – |
| Cont16 | – | – |
| Cont17 | – | – |

TABLE 2-continued

Examination of BRAF V600E Mutation Status in Melanoma Patient Plasma-Derived ExoDNA

|  | Tumor | exoDNA |
|---|---|---|
| Cont18 | − | − |
| Cont19 | − | − |
| Cont20 | − | − |
| Cont21 | − | − |
| Mel6 | − | − |
| Mel57 | − | + |
| Mel61 | + | − |
| Mel63 | − | + |
| Mel71 | + | + |
| Mel94 | − | − |
| Mel95 | + | + |
| Mel96 | − | − |
| Mel99 | − | − |
| Mel102 | + | − |
| Mel103 | + | − |
| Mel105 | + | + |

AS-PCR was employed to detect BRAF V600E mutation in exoDNA isolated from plasma of healthy control subjects ("Cont #") and melanoma patients ("Mel #") with known mutational status in primary tumor tissues.

Example 5

Mutational Analysis of Exosomal DNA in Cell Line and Clinical Samples of Non-Small Cell Lung Cancer The utility of exoDNA mutational analysis was also examined in a second tumor model, i.e., the non-small-cell lung cancer (NSCLC) model. Mutations in oncogene EGFR has been reported at high frequency in NSCLC (Lynch et al., "Activating Mutations in the Epidermal Growth Factor Receptor Underlying Responsiveness of Non-small-cell Lung Cancer to Gefitinib," *N Engl J Med* 350(21): 2129-39 (2004); Paez et al., "EGFR Mutations in Lung Cancer: Correlation with Clinical Response to Gefitinib Therapy," *Science* 304(5676): 1497-500 (2004); and Pao et al., "EGF Receptor Gene Mutations are Common in Lung Cancers From "Never Smokers" and are Associated with Sensitivity of Tumors to Gefitinib and Erlotinib," *Proc Natl Acad Sci USA* 101(36): 13306-11 (2004), which are hereby incorporated by reference in their entirety). In addition, many NSCLC patients have disease that is difficult to biopsy and/or the amount of tissue is insufficient for genotyping, limiting their treatment options. Thus, the development of alternative non-invasive diagnostic tests facilitating molecular diagnosis of NSCLC is of significant clinical interest.

The mutational status of EGFR was examined in exoDNA extracted from banked specimens of a small group of lung cancer patients whose EGFR mutational status had been examined in primary tumor tissue (see Table 3). Similar to the melanoma study, AS-PCR analysis of exon 19 deletion in exoDNA samples was consistent with exon 19 deletion analysis in 9 out of 14 primary tumor tissue samples. Exon 19 deletions were missed exoDNA samples from two patients that were positive for the deletion by primary tumor tissue analysis, and deletions were detected in exoDNA samples from three patients that were negative for the deletion by primary tumor tissue sample analysis. AS-PCR analysis of T790M mutational status in exoDNA samples was consistent in 11 out of 14 patient tumor tissue examined samples. T790M mutation detection was missed in 3 exoDNA samples. HRM analysis of L858R mutational status in exoDNA samples was consistent with primary tumor tissue samples for 9 of 14 patients. Two mutations were missed in exoDNA samples, while mutations were detected in exoDNA samples of three patients that were negative for the mutation by primary tumor tissue sample analysis.

TABLE 3

Examination of EGFR Mutation Status in NSCLC Patient Plasma-Derived ExoDNA.

| | Lung cancer samples | | | | | | | |
|---|---|---|---|---|---|---|---|---|
| | EGFR Exon 19 del | | | EGFR L858R | | EGFR T790M | | |
| | Tumor | exoDNA-AS-PCR | exoDNA-HRM | Tumor | exoDNA-HRM | Tumor | exoDNA-HRM | exoDNA-AS-PCR |
| 2 | | | | | + | | | |
| 5 | | | | | | | | |
| 9 | | + | | | + | | + | |
| 11 | | | | + | + | | ? | |
| 15 | | + | ? | + | + | + | | + |
| 17 | + | | | | + | | | |
| 22 | | + | + | + | + | | | |
| 48 | + | | | | | + | | |
| 51 | | | | + | | | + | |
| 52 | | | + | | | | | |
| 55 | + | + | + | | | + | + | + |
| 65 | | | + | + | | | | |
| 66 | | | | | + | | ? | |
| 73 | + | + | + | | | + | | |

ExoDNA was isolated from the plasma of NSCLC patients with known EGFR mutational status in primary tumor tissues. AS-PCR and HRM curve analysis were employed to detect deletion of exon 19, L858R point mutation, and T790M point mutation. "?" indicates questionable cases.

In conclusion, exoDNA phenocopies the mutational status of parental cells and has significant potential as a non-invasive, diagnostic and prognostic tool by offering the rapid genotyping of cancers enabling early detection of disease. Furthermore, diagnosis is feasible using this technique in cases when a biopsy is difficult to obtain (due to inaccessibility) or when a patient has multiple sites of disease. Moreover, this tool allows for frequent monitoring of the dynamics of tumor progression and molecular changes during treatment. The molecular diagnostic information gathered can guide therapeutic decisions. ExoDNA is likely more stable compared to free circulating nucleic acid due to the protection of exosomes from serum nucleases. Furthermore, enrichment of exosomes derived specifically from tumors is feasible through positive and/or negative immunoselection, which can enhance the quality of the specimen and the sensitivity of the mutational analysis. Finally, exosomes are secreted from tumors constitutively, and isolation of exosomes requires no special equipment. Therefore, an exoDNA-based test may be possible for all standard laboratories.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method comprising:

selecting a subject having cancer;

obtaining, from the selected subject, a sample containing exosomes;

isolating whole genomic DNA from the exosomes in the sample;

sequencing the isolated exosome derived whole genomic DNA; and detecting the presence or absence of the one or more genetic mutations in the exosome derived whole genomic DNA from the sample based on said sequencing to genotype the cancer of the subject.

2. The method of claim 1 further comprising:

selecting a suitable cancer therapeutic based on said detecting and administering the selected cancer therapeutic to said selected subject.

3. The method of claim 1, wherein the cancer is selected from the group consisting of melanoma, breast cancer, brain cancer, pancreatic cancer, ovarian cancer, colorectal cancer, liver cancer, renal cancer, prostate cancer, and lung cancer.

4. The method of claim 1, wherein the selected subject has melanoma and the presence or absence of a mutation in BRAF is detected.

5. The method of claim 4, wherein the detection of a mutation in BRAF is the detection of the presence of a V600E BRAF mutation.

6. The method of claim 1, wherein the one or more detected genetic mutations are in EGFR and are selected from the group consisting of an exon 19 deletion, L858R, T790M, and any combination thereof.

\* \* \* \* \*